(12) United States Patent
Kriesel et al.

(10) Patent No.: US 8,403,887 B2
(45) Date of Patent: Mar. 26, 2013

(54) FLUID DISPENSER

(76) Inventors: Marshall S. Kriesel, St. Paul, MN (US); Alan D. Langerud, Plymouth, MN (US); Donald B. Bivin, Oakland, CA (US); Joshua W. Kriesel, San Francisco, CA (US)

( * ) Notice: Subject to any disclaimer, the term of this patent is extended or adjusted under 35 U.S.C. 154(b) by 211 days.

(21) Appl. No.: 12/798,656

(22) Filed: Apr. 7, 2010

(65) Prior Publication Data
US 2011/0251556 A1    Oct. 13, 2011

(51) Int. Cl.
*A61M 37/00*   (2006.01)
(52) U.S. Cl. ...................................................... 604/132
(58) Field of Classification Search ................. 604/132, 604/131, 93.01, 80, 310, 306, 288.04, 288.01, 604/235, 217, 142, 185, 204, 214, 212
See application file for complete search history.

(56) References Cited

U.S. PATENT DOCUMENTS
7,828,770 B2 * 11/2010 Bivin et al. ................... 604/132

* cited by examiner

*Primary Examiner* — Manuel Mendez
(74) *Attorney, Agent, or Firm* — James E. Brunton

(57) ABSTRACT

A dispensing device for dispensing pain management medicaments to a patient comprises first and second threadably interconnectable sub-assemblies. The first of these sub-assemblies houses a fluid reservoir defining component while the second comprises a fluid delivery and control assembly that includes a novel flow control means that functions to control the flow of medicinal fluid from the fluid reservoir of the first sub-assembly toward the patient via strategically formed flow control passageways.

9 Claims, 28 Drawing Sheets

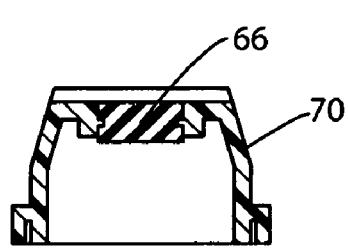
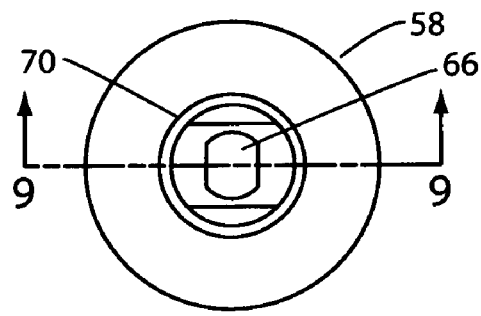
FIG. 8
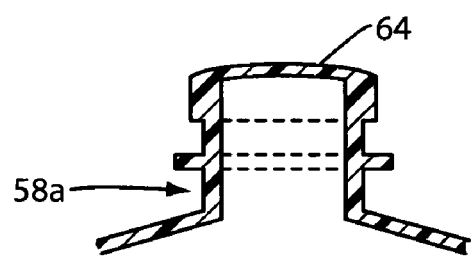
FIG. 10
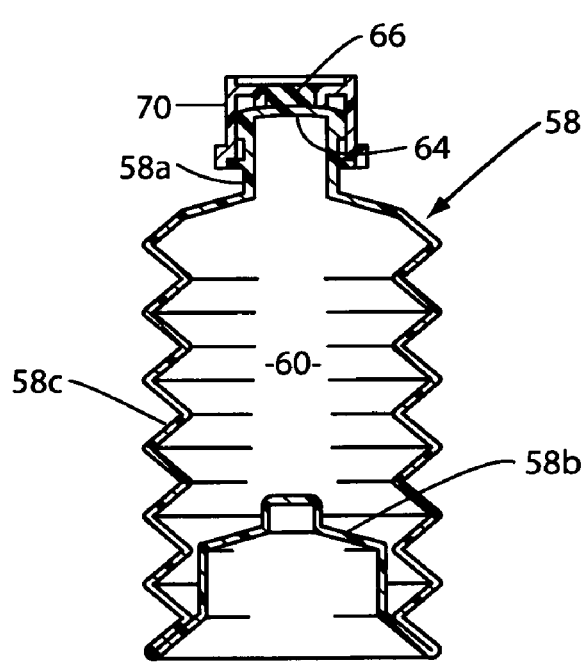
FIG. 9

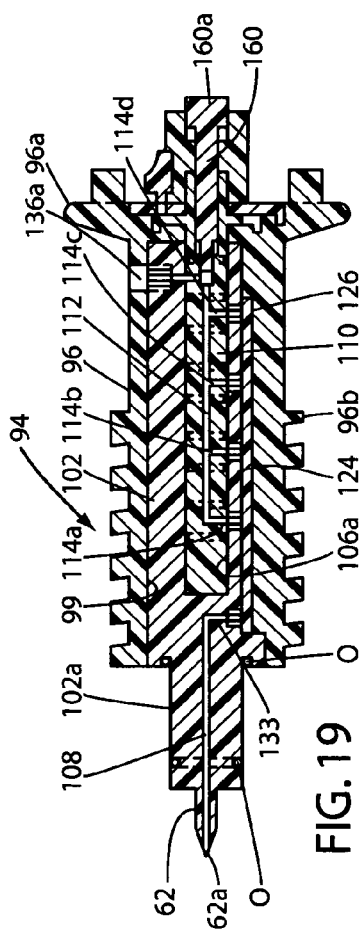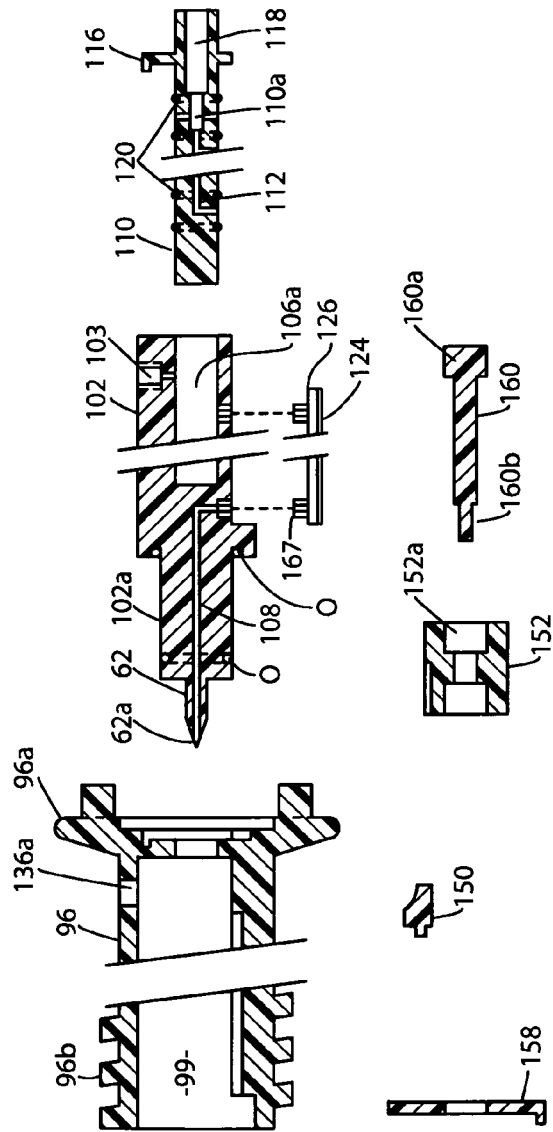
FIG. 19
FIG. 20

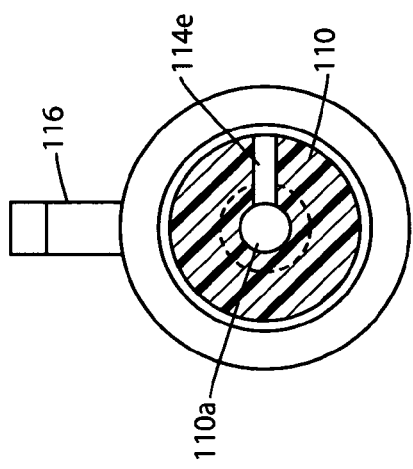
FIG. 24
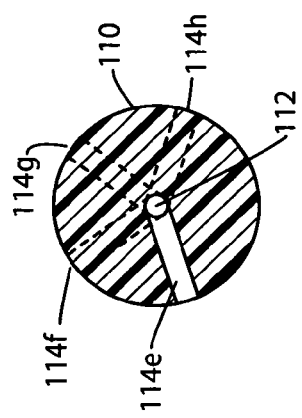
FIG. 23
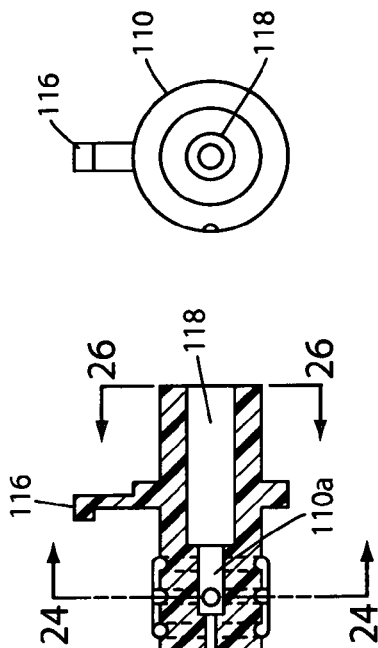
FIG. 26
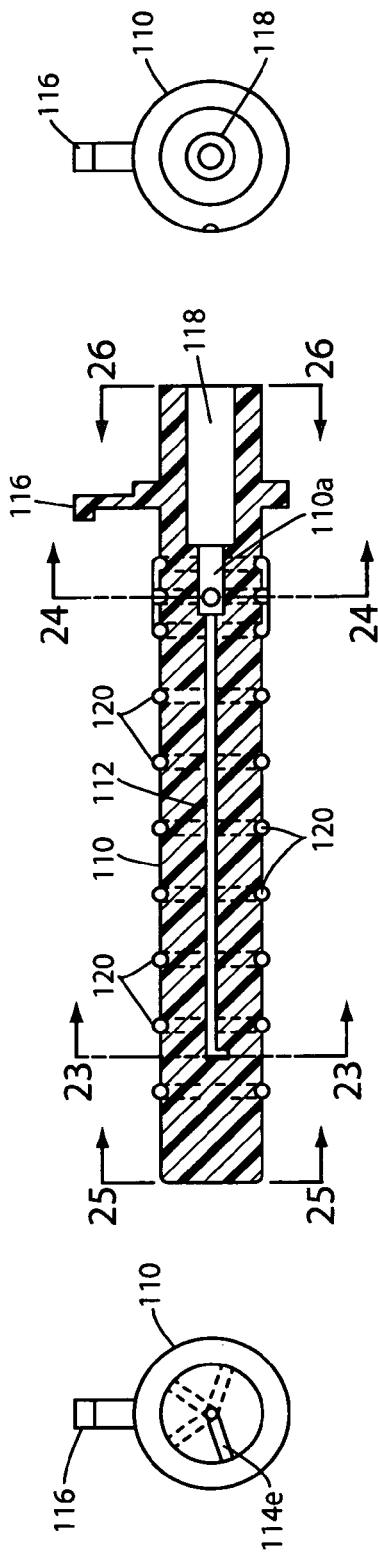
FIG. 22
FIG. 25

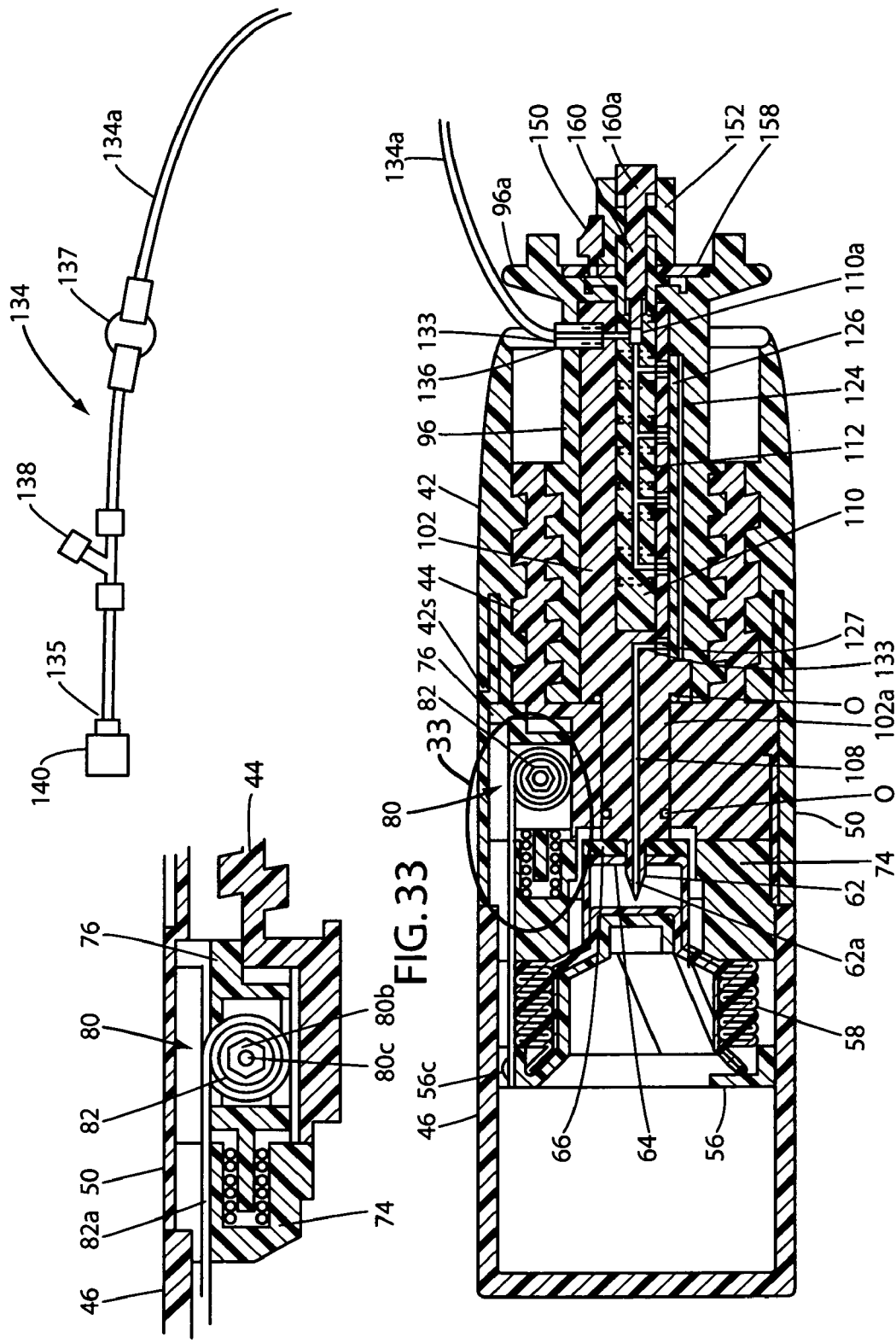

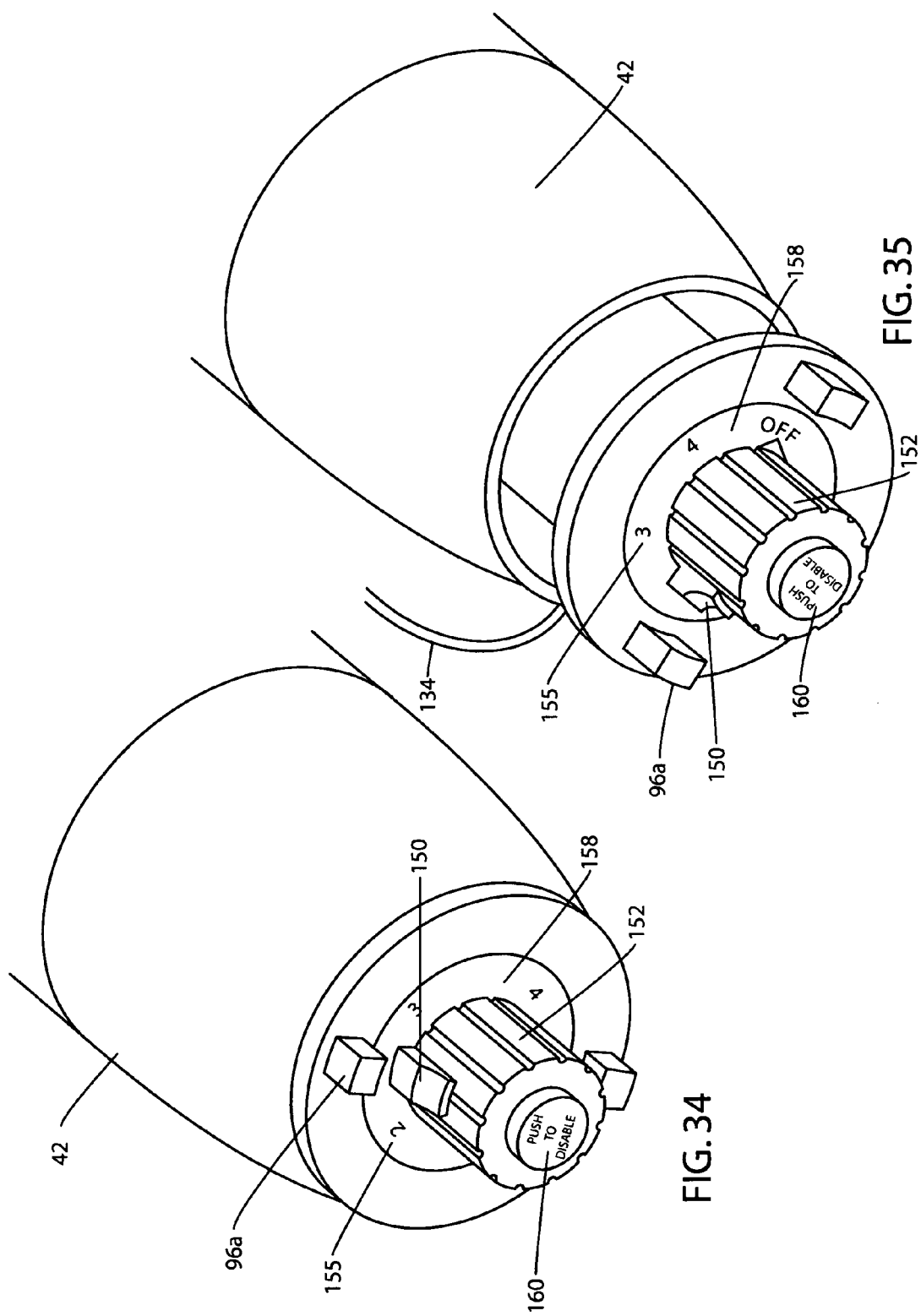

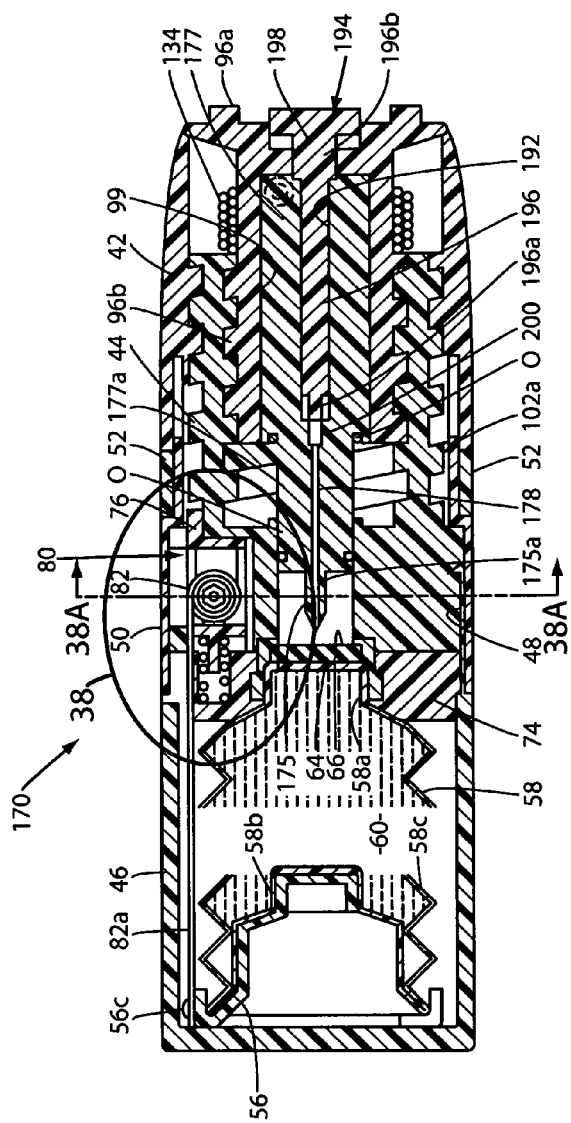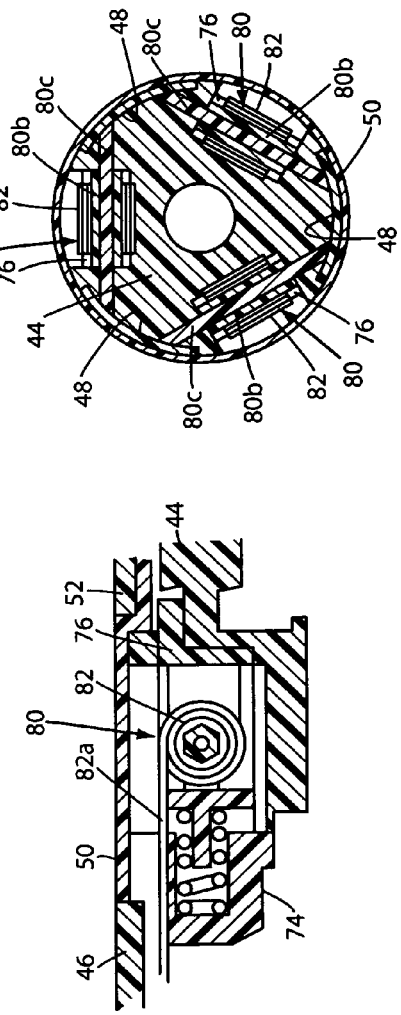
FIG. 37
FIG. 38A
FIG. 38

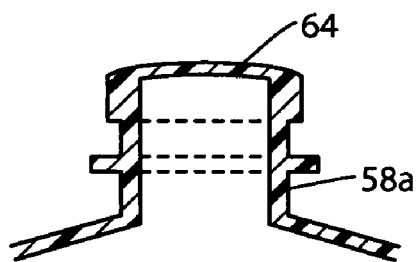
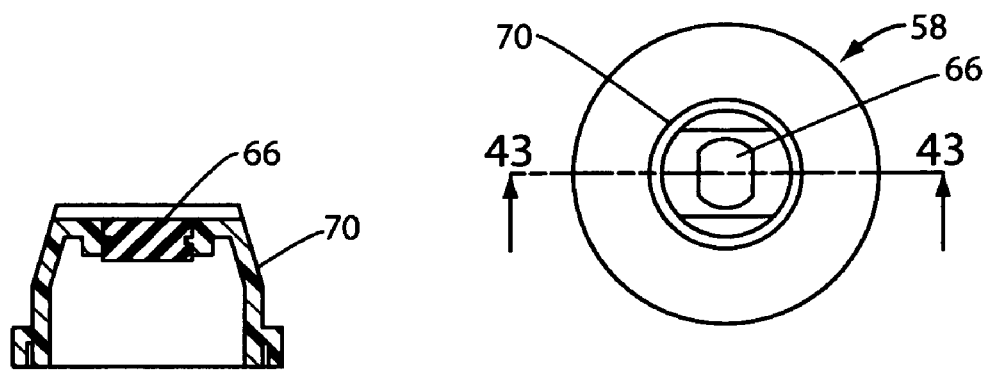
FIG. 42
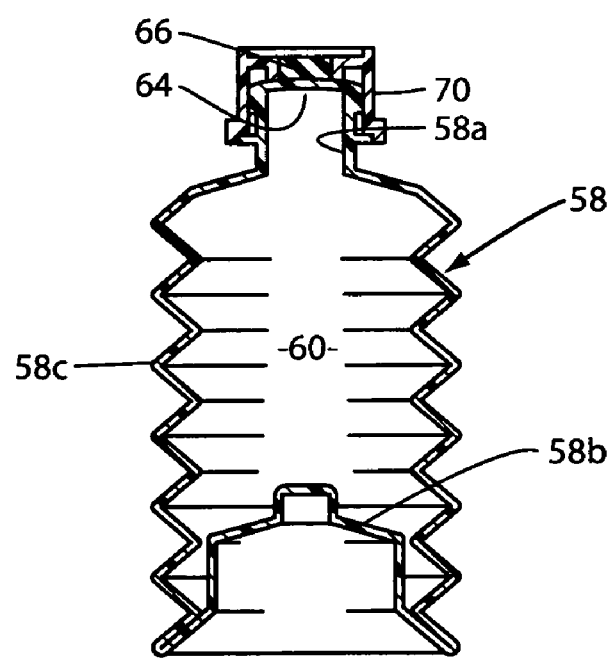
FIG. 44
FIG. 43

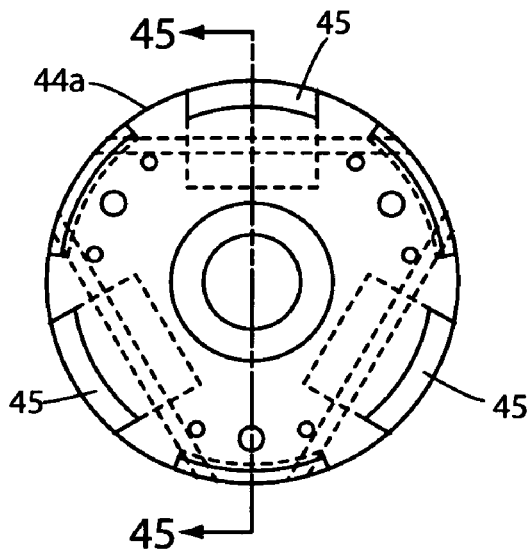
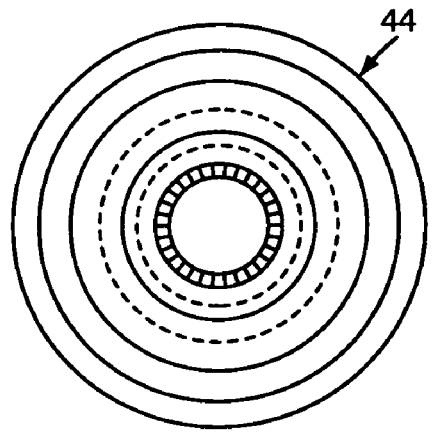
FIG. 46  FIG. 47
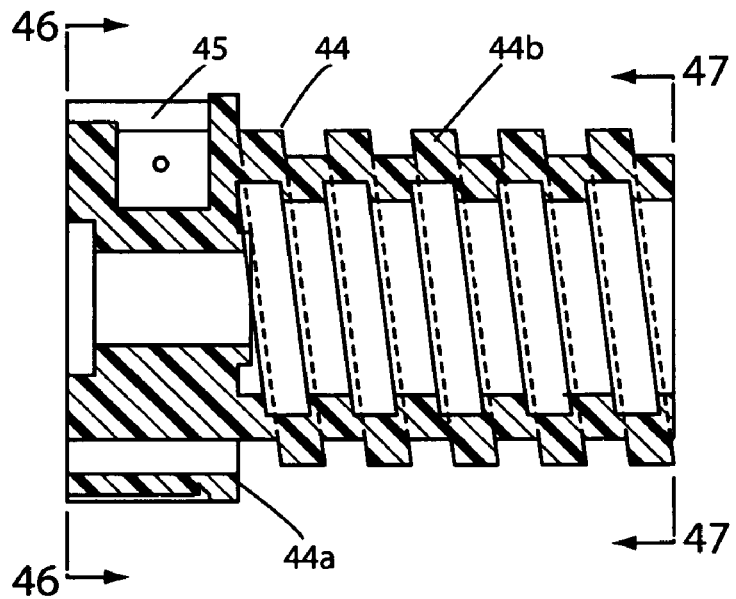
FIG. 45

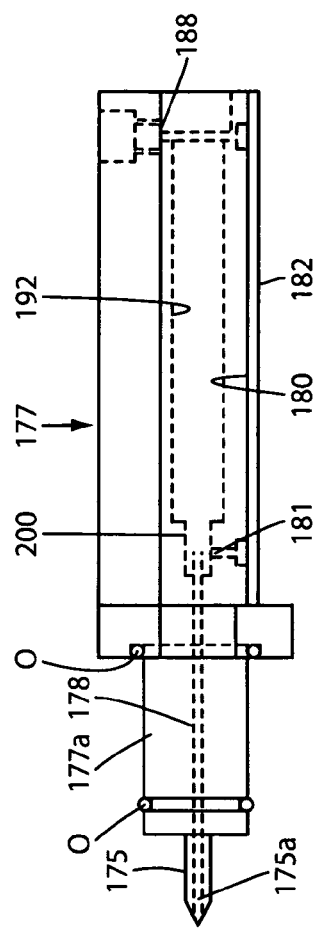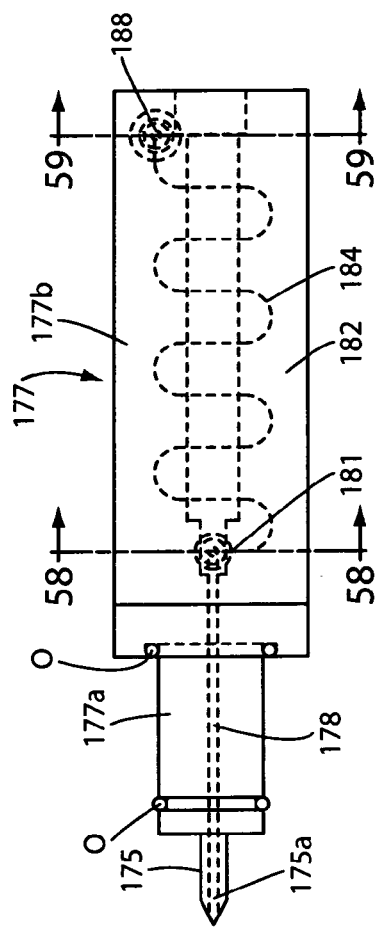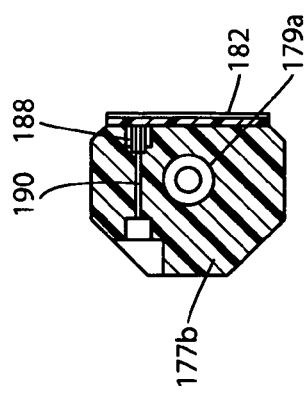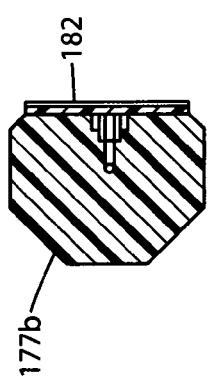
FIG. 56
FIG. 57
FIG. 59
FIG. 58

FLUID DISPENSER

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns a novel dispenser for dispensing medicinal fluids, such as Bupivacane to ambulatory patients that uniquely comprises a flow rate control system that regulates the pressure of medicaments flowing to the patient.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the dispensing device of the present invention for dispensing pain management medicaments to a patient comprises first and second threadably interconnectable sub-assemblies. The first of these sub-assemblies houses a fluid reservoir defining component while the second comprises a fluid delivery and control assembly that includes a novel flow control means that functions to control the flow of medicinal fluid from the fluid reservoir of the first sub-assembly toward the patient via a plurality of fluid flow control passageways.

By way of brief background, the fluid dispensing system of the present invention has been created to provide safe and efficacious drug and fluid delivery in hospitals, surgery centers, home care, austere environments, and other alternate sites of care. The fluid delivery systems are uniquely configured for use at the point-of-care and will allow drug or fluid infusion to be initiated during virtually any phase of care, in any healthcare setting, and continue uninterrupted, while en-route to other medical facilities or during rehabilitation.

Additionally, the self-contained and therapy-specific nature of the fluid delivery systems functions to reduce the probability of costly and potentially life-threatening medication errors. In this regard, the fluid delivery systems of the invention are consistent with the growing trend of unit-dosing, where clinicians, pharmacists and regulators agree that a "unit of use" is the preferred form of containerization for liquid and solid medicines to be administered in hospital, home, or alternate site settings. Unit-dose packaging is preferred because of its inherent ability to reduce the possibility of medication error, while promoting the use of bar coding at the point of care. The unit-dose drug delivery dispensers of the present invention are also equally well suited for use in the inpatient hospital environment, where surgeries that are more complex require longer recovery times, or cannot be sustained in a surgicenter setting, are still performed.

With the forgoing in mind, it is an object of the present invention to provide a novel, safe and efficacious drug and fluid delivery system that can be efficiently used in hospitals, surgery centers, home care, austere environments, and other alternate sites of care Another object of the invention is to provide a drug and fluid delivery system of the aforementioned character that is specifically configured for use at the point-of-care and one which will allow drug or fluid infusion to be initiated during virtually any phase of care, in any healthcare setting, and continue uninterrupted, while en-route to other medical facilities or during rehabilitation.

Another object of the invention is to provide a fluid dispensing system that can be used for controllably dispensing at a uniform rate a wide variety of fluid medicaments, such as Bupivacane, Ropivaciane, and Propofol and like medicinal.

Another object of the invention is to provide a pain management dispensing apparatus of the aforementioned character, of simple construction and one that can be used in the home care environment with a minimum amount of training.

Another object of the invention is to allow infusion therapy to be initiated quickly at the point of care without the assistance of a medical professional.

Another object of the invention is to provide a novel dispensing apparatus in which a stored energy source is provided in the form of a compressible, expandable or retractable member of novel construction that provides the force necessary to continuously and uniformly expel fluid from the device reservoir.

Another object of the invention is to provide a dispenser of the character described in the preceding paragraphs in which the stored energy source is provided in the form of a variable force spring that comprises a tightly coiled wound band of pre-hardened, perforated spring steel or stainless steel strip with built-in curvature so that each turn of the strip wraps tightly on its inner neighbor. When the strip is extended (deflected), the inherent stress resists the loading force the same as a common extension spring but at a variable rate.

Another object of the invention is to provide a dispenser of the class described which includes a fluid flow control assembly that precisely controls the flow of the medicament solution to the patient.

Another object of the invention is to provide a fluid dispensing apparatus that enables precise variable flow rate selection.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

BRIEF DESCRIPTION OF SEVERAL VIEWS OF THE DRAWINGS

FIG. 8 is a top plan view of one form of the closed container of the apparatus of the invention.

FIG. 9 is a cross-sectional view taken along lines 9-9 of FIG. 8.

FIG. 10 is an enlarged, exploded view of the upper portion of the container shown in FIG. 9 of the drawings.

FIG. 19 is a cross-sectional view of one form of the rate control and advancement housing of the apparatus of the invention.

FIG. 20 is a cross-sectional, exploded view of the rate control and advancement housing shown in FIG. 19.

FIG. 22 is a cross-sectional view of one form of the rate control shaft of the rate control assembly of the apparatus of the invention.

FIG. 23 is a cross-sectional view taken along lines 23-23 of FIG. 22.

FIG. 24 is a view partly in cross section taken along lines 24-24 of FIG. 22.

FIG. 25 is a view taken along lines 25-25 of FIG. 22.

FIG. 26 is a view taken along lines 26-26 of FIG. 22.

FIG. 32 as a longitudinal cross-sectional view similar to FIG. 31, but showing the front housing rotated into a second position to place the apparatus in a fluid delivery configuration.

FIG. 33 is an enlarged cross-sectional view of the area designated as "33" in FIG. 32.

FIG. 34 is an enlarged fragmentary perspective front view of the apparatus shown in FIG. 2 of the drawings illustrating the configuration of the rate control and disable mechanisms of the invention when the device is in a non-operating condition.

FIG. 35 is an enlarged fragmentary perspective front view of the apparatus shown in FIG. 34 of the drawings illustrating the configuration of the rate control and disable mechanisms of the invention when the device is in an operating condition.

FIG. 37 is a longitudinal cross-sectional view of a fluid dispensing apparatus shown in FIG. 36 of the drawings.

FIG. 38 is a fragmentary cross-sectional view of the area designated as 38 in FIG. 37.

FIG. 38A is a cross-sectional view taken along lines 38A-38A of FIG. 37.

FIG. 42 is a top plan view of the closed container of this latest form of the invention.

FIG. 43 is a cross-sectional view taken along lines 43-43 of FIG. 42.

FIG. 44 is an enlarged, exploded view of the upper portion of the container shown in FIG. 43 of the drawings.

FIG. 45 is an enlarged cross-sectional view taken along the lines 45-45 of FIG. 46.

FIG. 46 is a view taken along lines 46-46 of FIG. 45.

FIG. 47 is a view taken along lines 47-47 of FIG. 45.

FIG. 56 is a top plan view of the rate control and advancement housing of this latest form of the invention.

FIG. 57 is a side elevational view of the rate control and advancement housing shown in FIG. 56.

FIG. 58 is a cross-sectional view taken along lines 58-58 of FIG. 57.

FIG. 59 is a view partly in cross section taken along lines 59-59 of FIG. 57.

DETAILED DESCRIPTION OF THE INVENTION

Definitions

Figure 1:
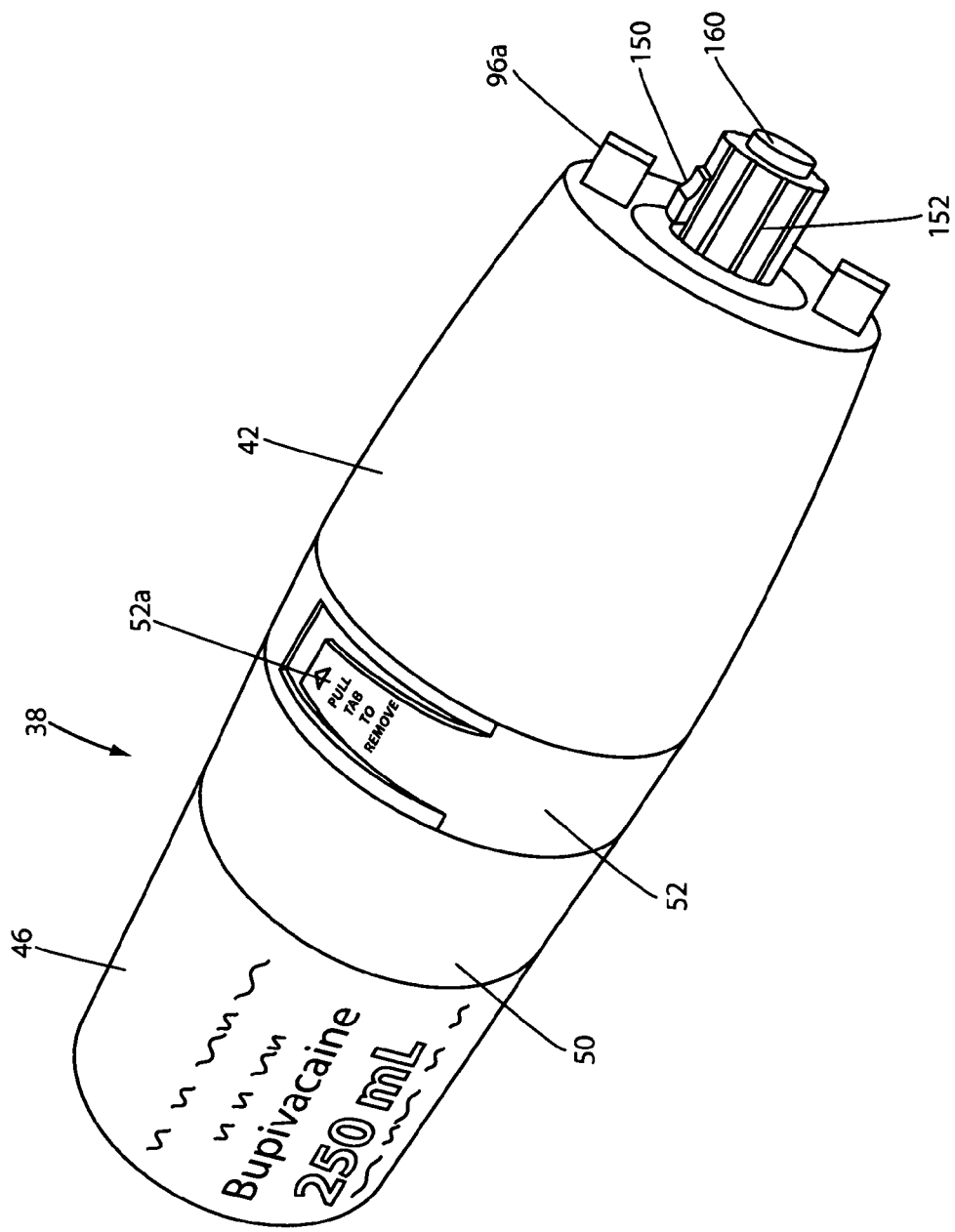
FIG. 1 is a generally perspective view of one form of the fluid dispensing apparatus of the present invention.
Figure 4:
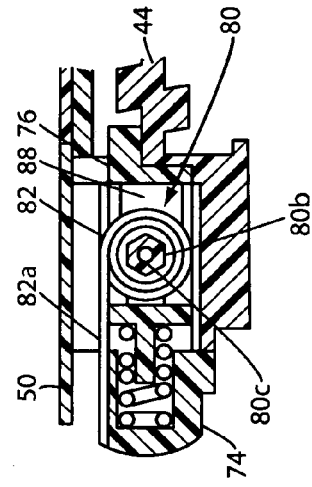
FIG. 4 is an enlarged cross-sectional view of the area designated as "4" In FIG. 2.

As used herein the following terms mean:
Unitary Container:
A closed container formed from a single component.
Continuous/Uninterrupted Wall:
A wall having no break in uniformity or continuity.
Hermetically Sealed Container:
A container that is designed and intended to be secure against the entry of microorganisms and to maintain the safety and quality of its contents after pressurizing.
Aseptic Processing:
The term 'aseptic processing' as it is applied in the pharmaceutical industry refers to the assembly of sterilized components and product in a specialized clean environment.
Sterile Product:
A sterile product is one that is free from all living organisms, whether in a vegetative or spore state.
Blow-Fill-Seal Process:
The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Collapsible Container:
A dispensing apparatus in which one or more walls of the container are made of a material which will deform (collapse) when pressure is applied thereto; or a dispensing apparatus having a collapsible or telescoping wall structure.
Constant Force Spring:
Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.
Modified Constant Force Spring (Variable Force Spring):
The modified constant force spring or variable force spring of the present invention comprises a spring of highly novel configuration that includes an elongated, pre-stressed strip of spring material that may be metal, a polymer, a plastic, or a composite material with built-in curvature so that, like the conventional constant force spring, each turn of the strip wraps tightly on its inner neighbor. Uniquely, in one form of the invention the elongated pre-stressed strip of spring material exhibits a cross-sectional mass that varies along said length. This variation in cross-sectional mass along the length of the spring can be achieved in various ways, as for example, by varying the width of the pre-stressed strip along its length and by providing spaced-apart apertures in the pre-stressed strip along its length. In another form of the invention, the pre-stressed strip of spring material is coiled about the spring drum to predetermined varying degrees of tightness. Accordingly, similar to the variable force spring having a variation in cross-sectional mass along the length of the spring, a variation of coil tightness can produce highly specific and desirable linear and non-linear force-distention curves.

Figure 3:
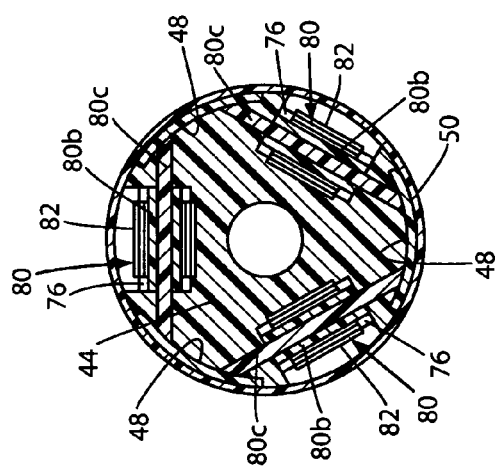
FIG. 3 is a cross-sectional view taken along lines 3-3 of FIG. 2.
Figure 2:
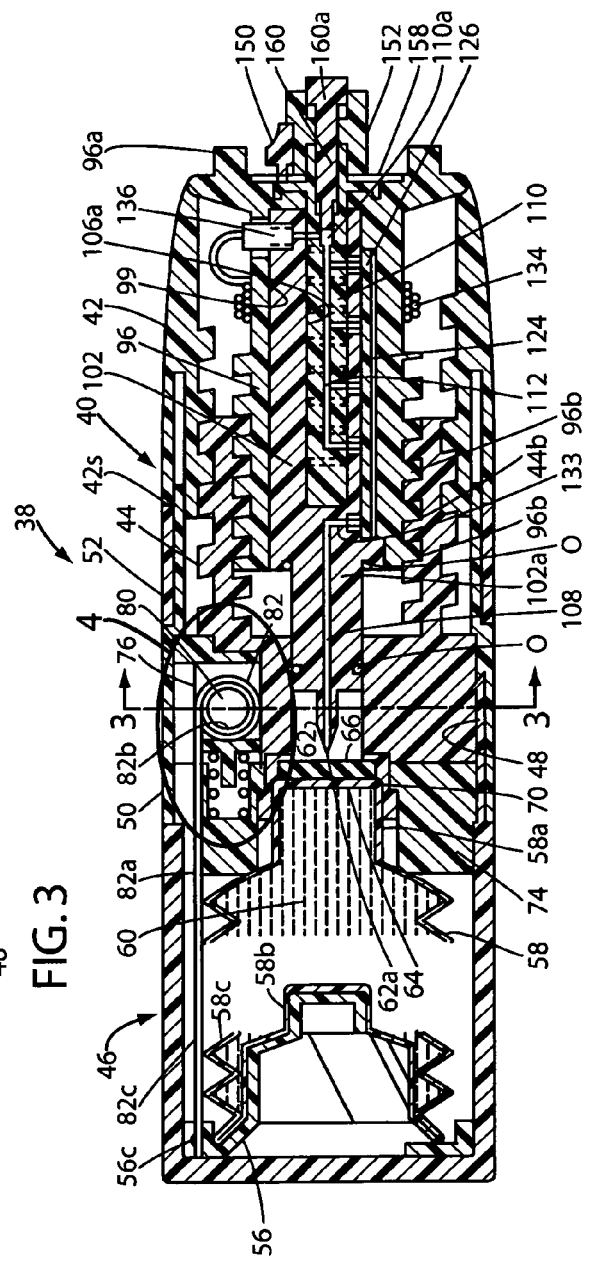
FIG. 2 is a longitudinal cross-sectional view of a fluid dispensing apparatus shown in FIG. 1 of the drawings.

Referring to the drawings and particularly to FIGS. 1 and 2, one form of the fluid dispensing apparatus of the present invention for dispensing medicaments to a patient is there shown and generally designated by the numeral 38. As best seen in FIG. 2, the fluid dispensing apparatus here comprises a first assembly 40 that includes an internally threaded first, or front housing 42 and an internally-externally threaded second or reservoir spring housing 44 connected to the internally threaded front housing 42. Fluid dispensing apparatus 38 also includes a second assembly 46 that is connected to the internally-externally threaded reservoir spring housing 44 of the first assembly 40 by three circumferentially spaced locking tabs 48 (FIG. 3). Located between the first and second assemblies 40 and 46 is a separator collar 50 and disposed between separator collar 50 and front housing 42 is a tear strip, or locking band 52, the purpose of which will presently be described.

Housed within second assembly 46 and carried by a carriage 56 is a fluid reservoir defining component here shown as a hermetically sealed collapsible container 58. Operably associated with the carriage 56 for moving it between a first retracted position shown in FIG. 2 and a second advanced, fluid delivery position shown in FIG. 32 is a novel stored energy means, the character of which will presently be described. As best seen by referring to FIGS. 5, 6 and 7, carriage 56 includes a base 56a, an outwardly extending reservoir receiving body 56b and a plurality of spring securement subassemblies 56c that are connected the base 56a. The details of construction of spring securement subassemblies 56c will be described in the paragraphs which follow.

As best seen in FIGS. 2, 5 and 8 through 10, reservoir defining component 58 here comprises an integrally formed, hermetically sealed container that includes a fluid medicament reservoir 60. Integrally formed reservoir defining component 58 includes a front portion 58a, a rear, inwardly extending, ullage defining wall portion 58b and a collapsible accordion-like, continuous, uninterrupted side wall 58c that interconnects the front and rear portion of the container. In a manner presently to be described, fluid medicament reservoir 60 is accessible via a penetrating member 62 which forms the inlet to the fluid delivery and control assembly of the invention, the character of which will presently be described. More particularly, penetrating member 62, that forms a part of the penetrating housing of the invention, is adapted to pierce a top, or closure wall 64 of the reservoir defining component 58 as well as a pierceable septum 66 (FIGS. 2, 8, 9 and 10) which is secured in position over closure wall 64 by means of a closure cap 70 that is affixed to the neck portion 58a of the reservoir defining component.

The reservoir defining component 60 is uniquely formed using an aseptic blow fill technique and the reservoir portion of the container is sealed by the thin closure or top wall 64. The continuously formed top, bottom and accordion sidewalls cooperate to define sealed medicament reservoir 60. Prior to heat sterilization of the container, the piercable septum 66 is positioned over the closure wall and the closure cap 70 is positioned over the piercable septum and is secured to the neck portion 58a by any suitable means such as adhesive bonding, sonic welding or heat welding. The container is held in position within housing 46 by means of a ring like member 74 that is disposed in engagement with internally-externally threaded reservoir spring housing 44 in the manner shown in FIG. 2.

Ring-like member 74 functions to partially support three circumferentially spaced spring carriage assemblies 76, each of which houses a portion of the previously mentioned stored energy means of the invention (FIG. 3). More particularly, the spring carriage assemblies 76 house the drum assemblies 80 of the stored energy means about which a portion of the elongated springs 82 of the stored energy means are wound. Spring carriage assemblies 76 form a part of the spring retaining means of the invention that functions to initially retain the variable force springs in their extended position and then, upon rotation of said first assembly 40 relative to said second assembly 46, to permit said variable force springs to retract and in so doing move carriage 56 between the first retracted position shown in FIG. 2 and the second advanced, fluid delivery position.

By way of background, conventional constant force springs are a special variety of extension spring. They comprise tightly coiled wound bands of pre-hardened spring steel or stainless steel strip with built-in curvature so that each turn of the strip wraps tightly on its inner neighbor. When the strip is extended (uncoiled), the inherent stress resists the loading force the same as a common extension spring, but at a nearly constant (zero) rate.

In the present form of the invention, the stored energy means comprises three variable force spring assemblies that are somewhat similar to the prior art constant force springs, but uniquely comprise assemblies, the details of which will presently be described, in which the elongated band or strip portion 82a of the spring 82 is coiled about the spring drum 80b in predetermined varying degrees of tightness. In this way, the springs can produce highly specific and desirable linear and non-linear force-distention curves to meet the fluid delivery requirements of the invention.

Figure 6:
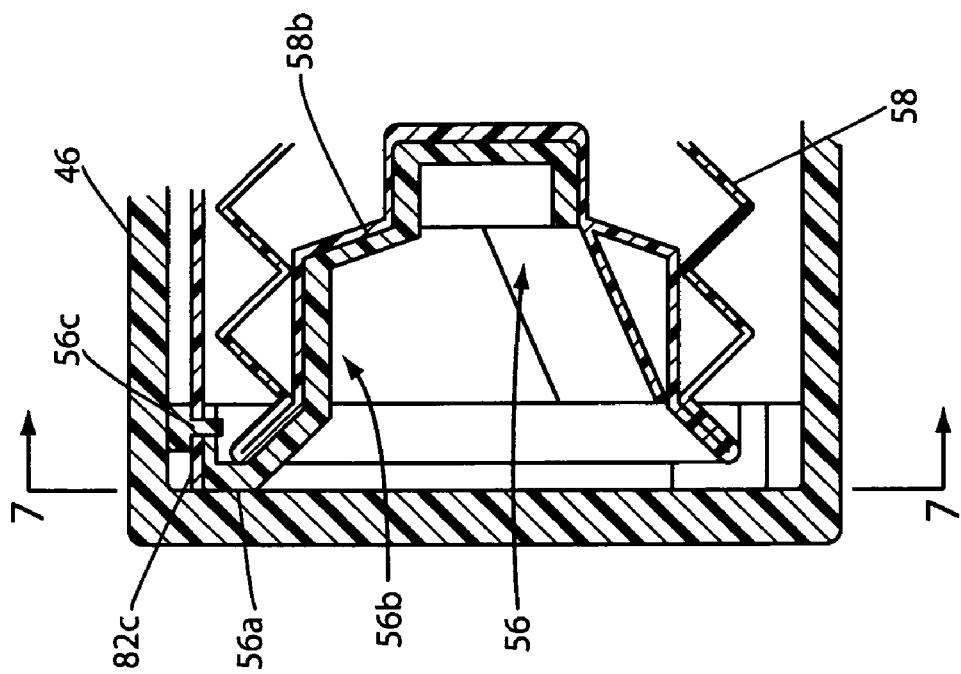
FIG. 6 is a greatly enlarged cross-sectional view of the left-hand portion of the apparatus shown in FIG. 2 of the drawings illustrating the construction of the carriage assembly of the invention.
Figure 7:
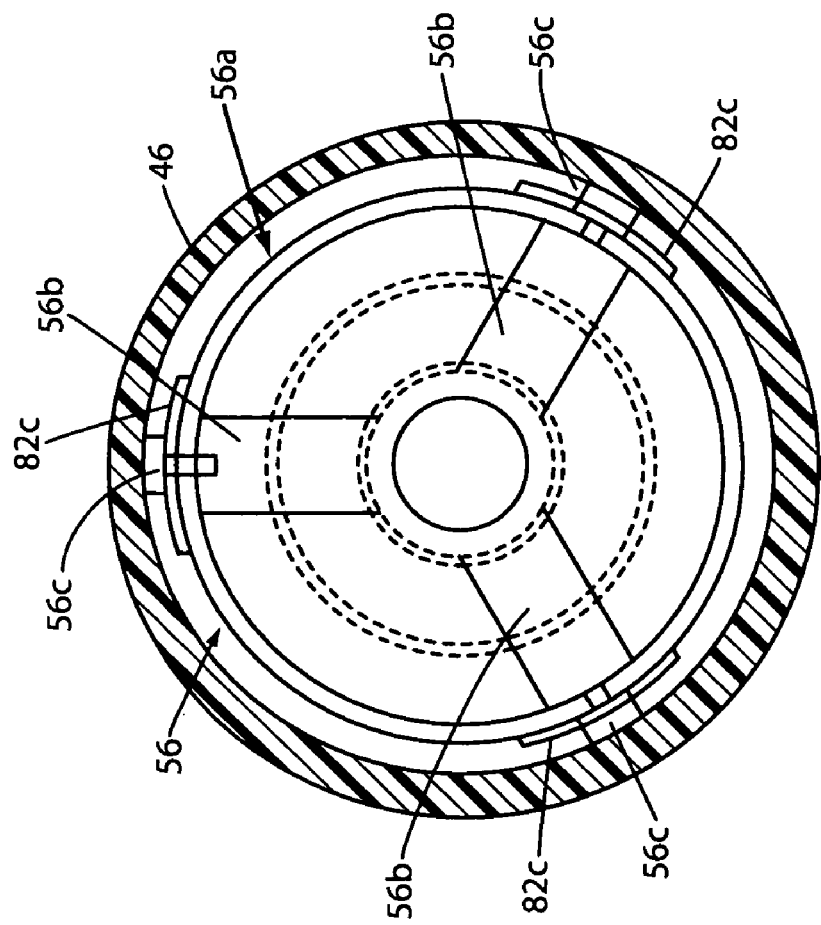
FIG. 7 is a cross-sectional view taken along lines 7-7 of FIG. 6.
Figure 12:
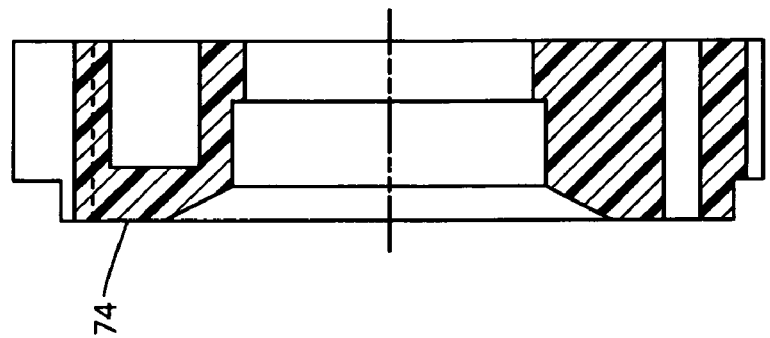
FIG. 12 is a cross-sectional view taken along lines 12-12 of FIG. 11.
Figure 11:
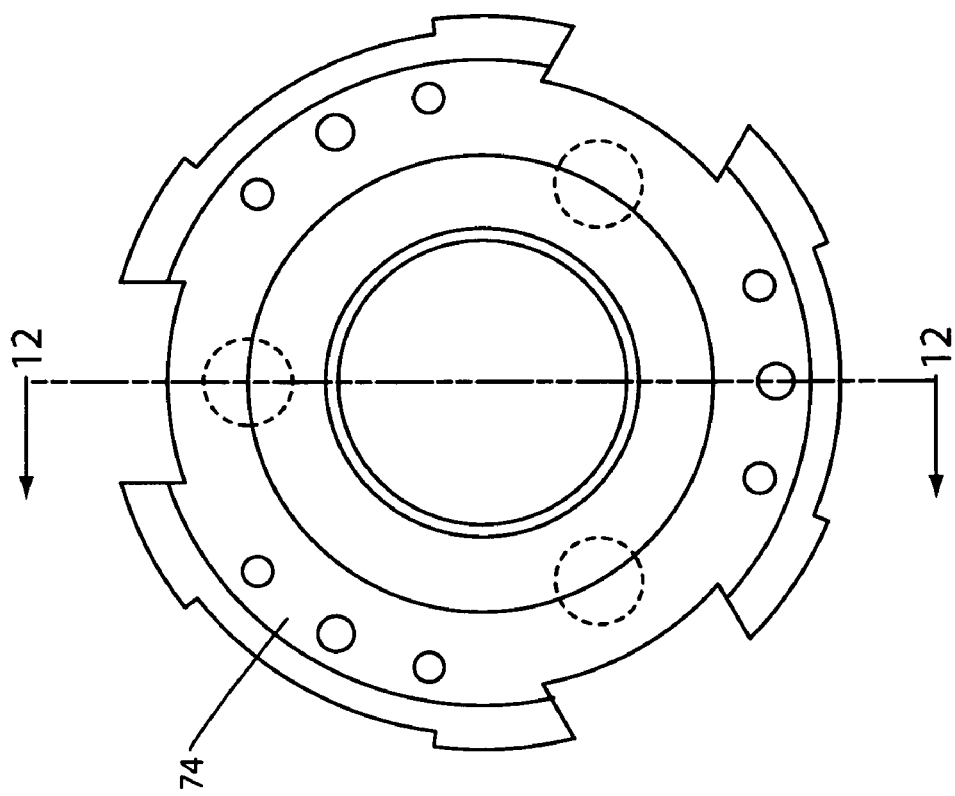
FIG. 11 is a rear view of the spring housing front member of the apparatus.

As best seen in FIG. 2, springs 82 are mounted with one end 82b tightly wrapped about drum assemblies 80 that are housed within spring carriage assemblies 76 and the other end 82c attached to carriage 56 by spring clamping members 56c in the manner shown in FIGS. 2, 6 and 7.

Figure 5:
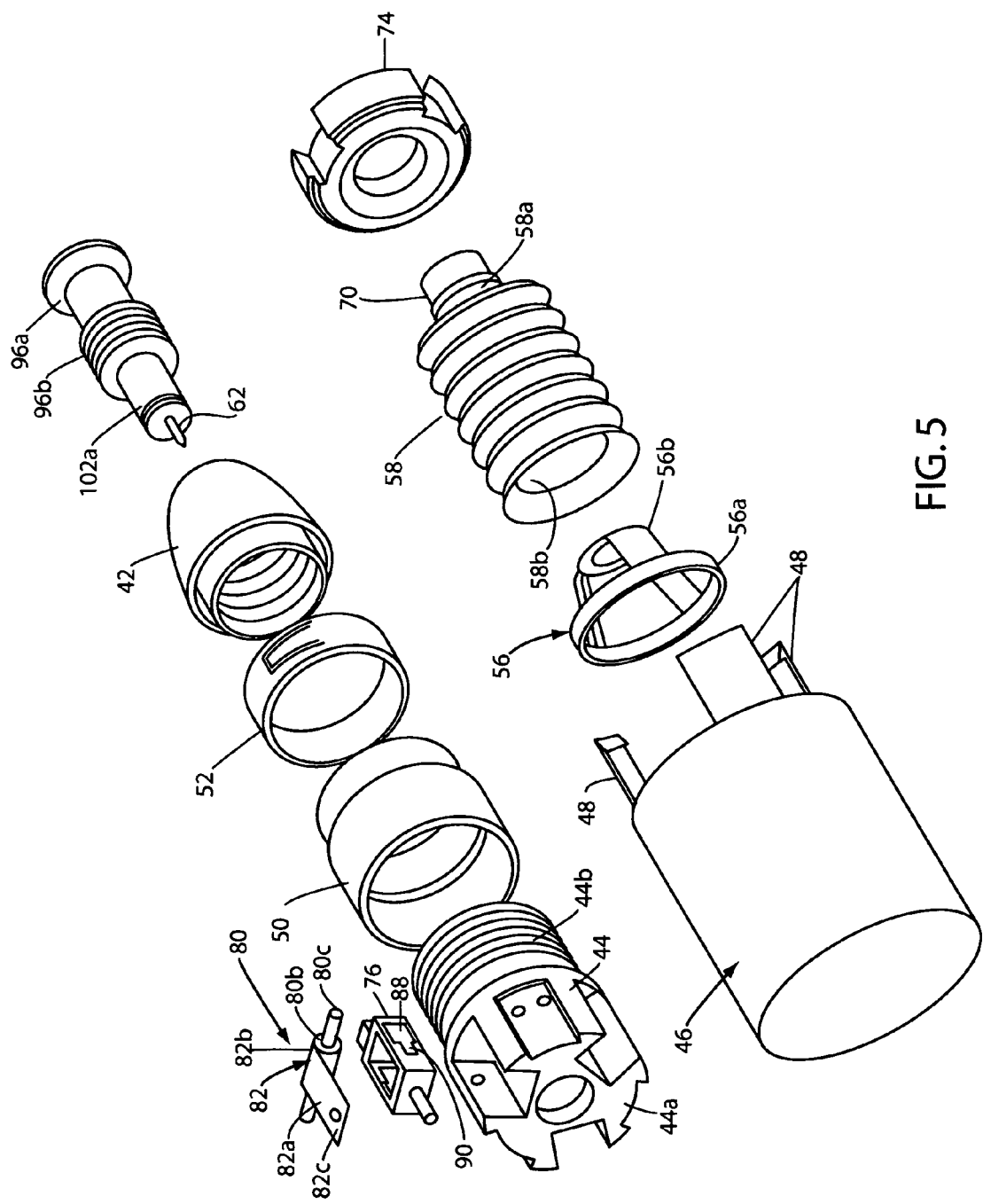
FIG. 5 is a generally perspective, exploded view of a fluid dispensing apparatus shown in FIG. 1.

Referring particularly to FIGS. 2, 3, 4 and 5 of the drawings, the configuration of the three identical, circumferentially spaced drum assemblies 80 is there illustrated. As indicated in FIGS. 3 and 5, each of the drum assemblies 80 is mounted within a selected one of the spring carriage assemblies 76 so that the shaft portion 80c of the drum assembly extends through openings provided in the side walls of the spring housings. More particularly, as indicated in the drawings, each of the sidewalls of each of the spring carriage assemblies 76 is provided with a generally rectangular shaped opening 88 and a smaller, generally rectangular shaped opening 90 that is in communication with the opening 88. When the shaft portion 80c of the spring assembly extends through the smaller opening 90, rotation of the drum is prevented. However, as will presently be discussed, when the spring housings are urged into a second, rearward position as a result of relative rotation of housings 42 and 44, drum 80b is free to rotate so that the spring can be wound about the drum thereby urging the carriage 76 forwardly of the apparatus.

Figure 14:
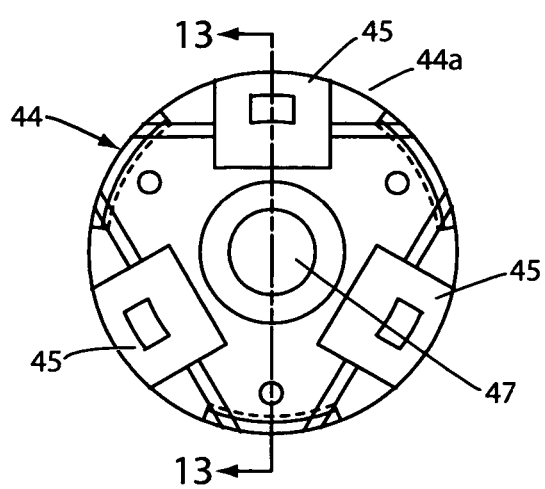
FIG. 14 is a view taken along lines 14-14 of FIG. 13.
Figure 15:
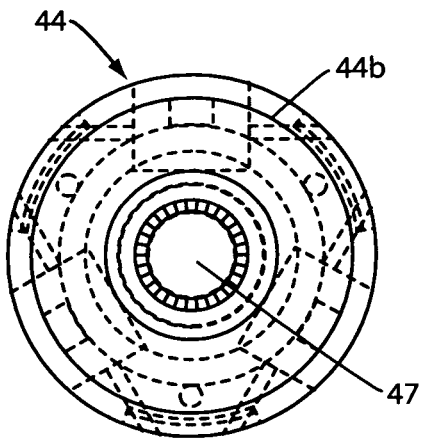
FIG. 15 is a view taken along lines 15-15 of FIG. 13.
Figure 13:
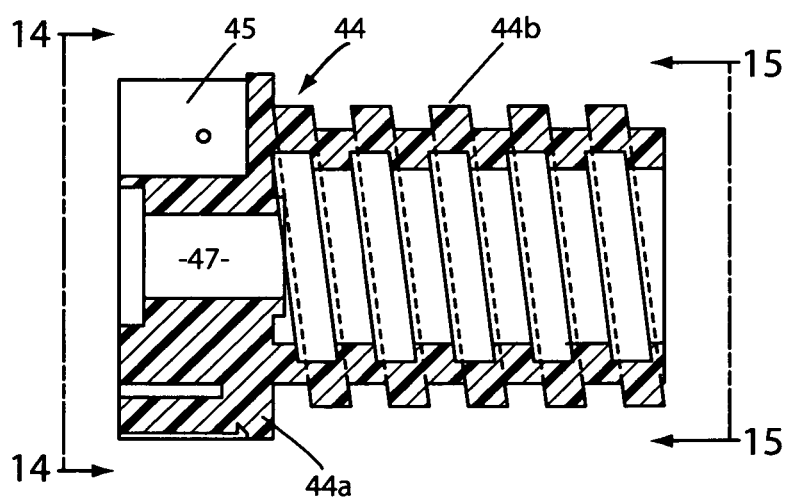
FIG. 13 is an enlarged cross-sectional view taken along lines 13-13 of FIG. 14.
Figures 16, 16A:
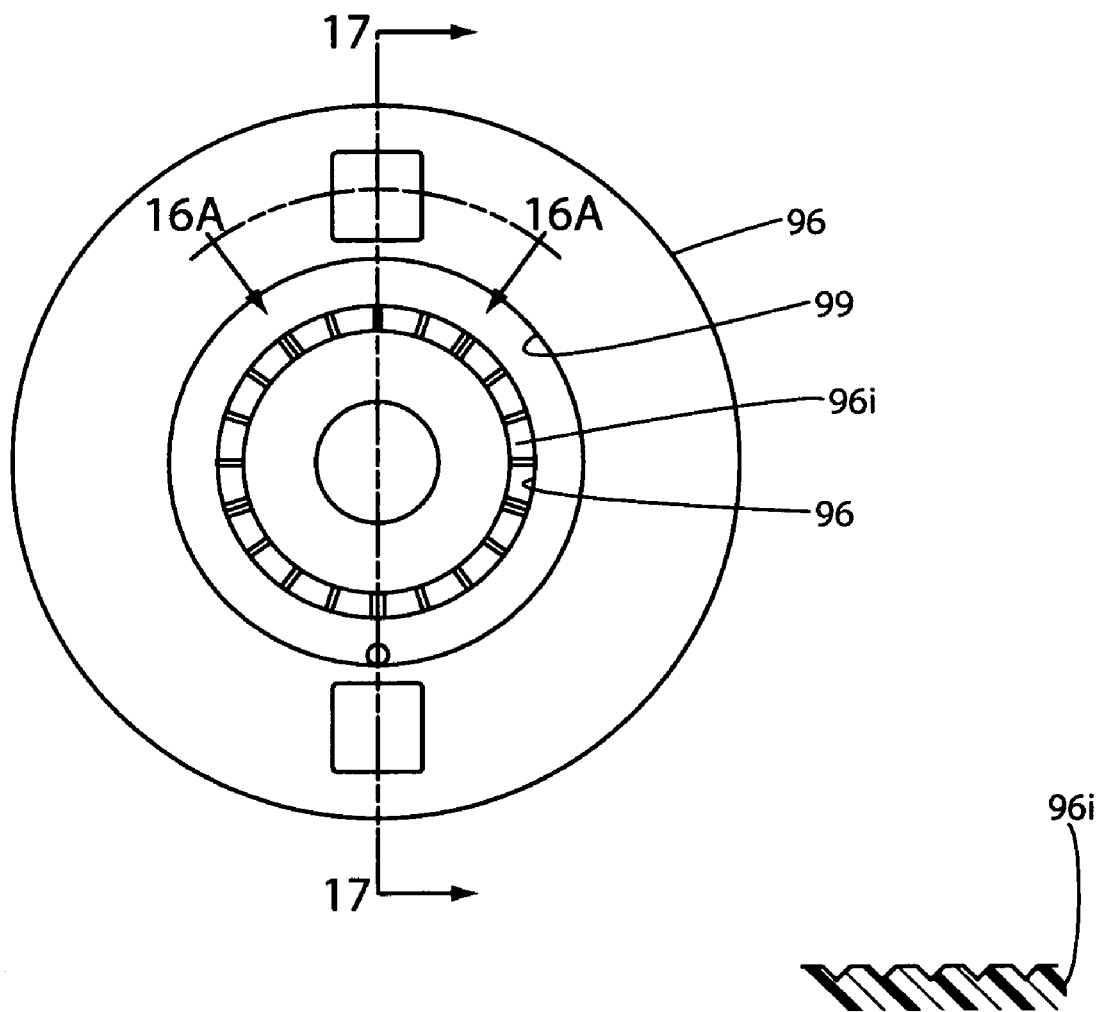
FIG. 16 is a front view of the rate control advancement housing of the apparatus of the invention.
FIG. 16A is a view taken along lines 16A-16A of FIG. 16.

As previously mentioned, ring-like member 74 functions to partially support three circumferentially spaced spring carriage assemblies 76. As indicated in the drawings, internally-externally threaded reservoir spring housing 44 also functions to partially support the three circumferentially spaced spring carriage assemblies 76. In this regard, reservoir spring housing 44, the details of construction of which are illustrated in FIGS. 13, 14 and 15 of the drawings, is provided with a rearward body portion 44a to which the three circumferentially spaced locking tabs 48 are connected and a forward end currently-externally threaded reduced diameter portion 44b. As best seen in FIG. 14, body portion 44a is provided with three circumferentially spaced cavities 45 within which portions of the spring carriage assemblies 76 are received. Body portion 44a is also provided with a central bore 47 that receives a portion of the important fluid delivery and control means of the invention.

Figure 18:
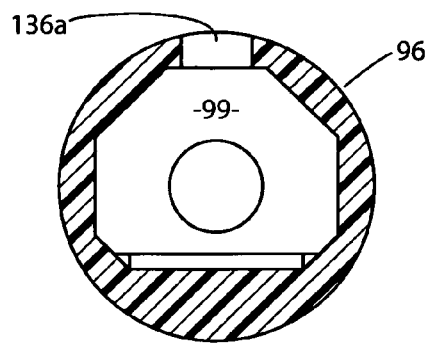
FIG. 18 is a cross-sectional view taken along lines 18-18 of FIG. 17.
Figure 17:
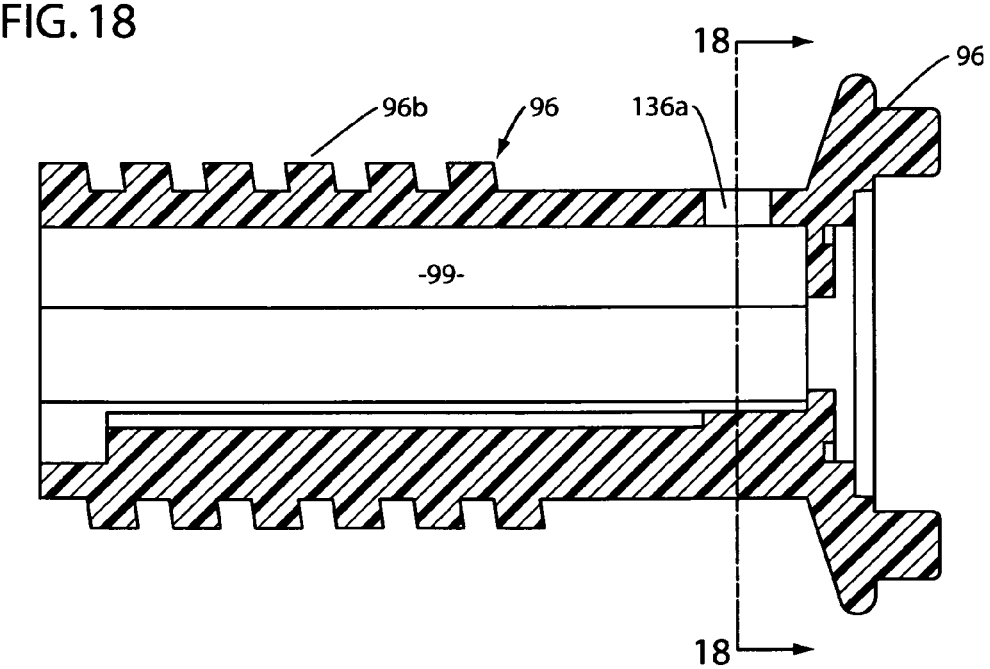
FIG. 17 is an enlarged cross-sectional view taken along lines 17-17 of FIG. 16.

Considering next the fluid delivery and control means of the invention, this important means, which functions to control the flow of fluid from the fluid reservoir of the collapsible container toward the patient, comprises a flow control assembly generally designated in the drawings by the numeral 94. Assembly 94 includes a rate control advancement housing 96 the character of which is illustrated in FIGS. 17 and 18. Housing 96 includes an enlarged diameter finger gripping portion 96a and a reduced diameter, externally threaded portion 96b. Externally threaded portion 96b is provided with central bore 99 which receives a penetrating assembly 102 that includes the previously identified penetrating member 62 that has a fluid passageway 62a. Penetrating assembly 102 includes a body portion 102a having a fluid passageway 108 and a central bore 106a that rotatably receives a rate control shaft 110. Rate control shaft 110 has a central fluid passageway 112 and a plurality of longitudinally spaced radial passageways 114e, 114f, 114g and 114h that communicate with central fluid passageway 112 (FIGS. 23 and 25). Rate control shaft 110 also has an outwardly extending indexing tab 116 and a central bore 118 that are in communication with central fluid passageway 112. Indexing tab is receivable within a groove 96g, which is formed in the face of the adjacent housing, which groove is provided with circumferentially spaced indexing grooves 96i. A plurality of O-rings 120 circumscribe the rate control shaft and sealably engage the inner wall of central bore 106a so as to prevent fluid leakage between the rate control shaft and body portion 106a of the penetrating assembly 102.

Figure 20A:
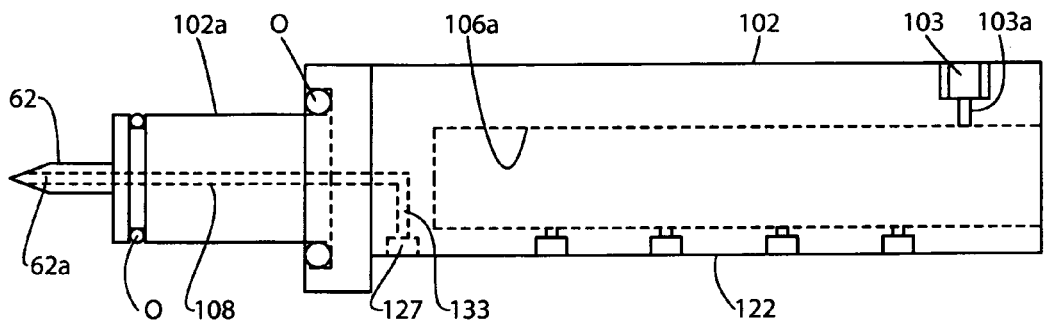
FIG. 20A is a top view of one form of the penetrating assembly of the apparatus of the invention.
Figure 20B:
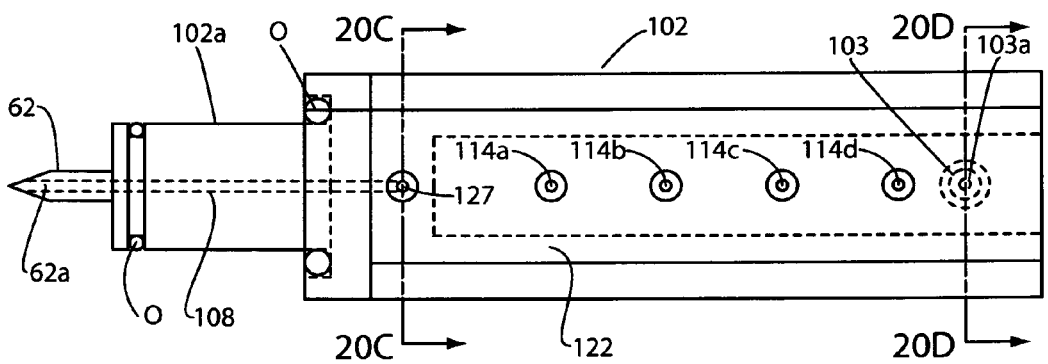
FIG. 20B is a side view of FIG. 20A.
Figure 20C:
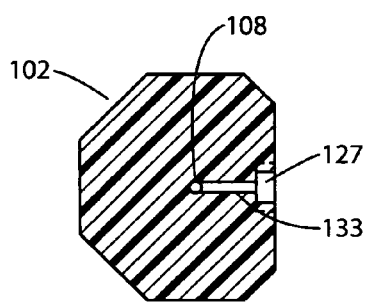
FIG. 20C is a view taken along lines 20C-20C of FIG. 20B.
Figure 20D:
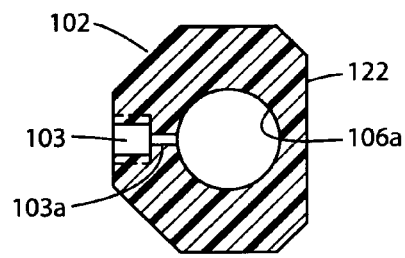
FIG. 20D is a view taken along lines 20D-20D of FIG. 20B.
Figure 21:
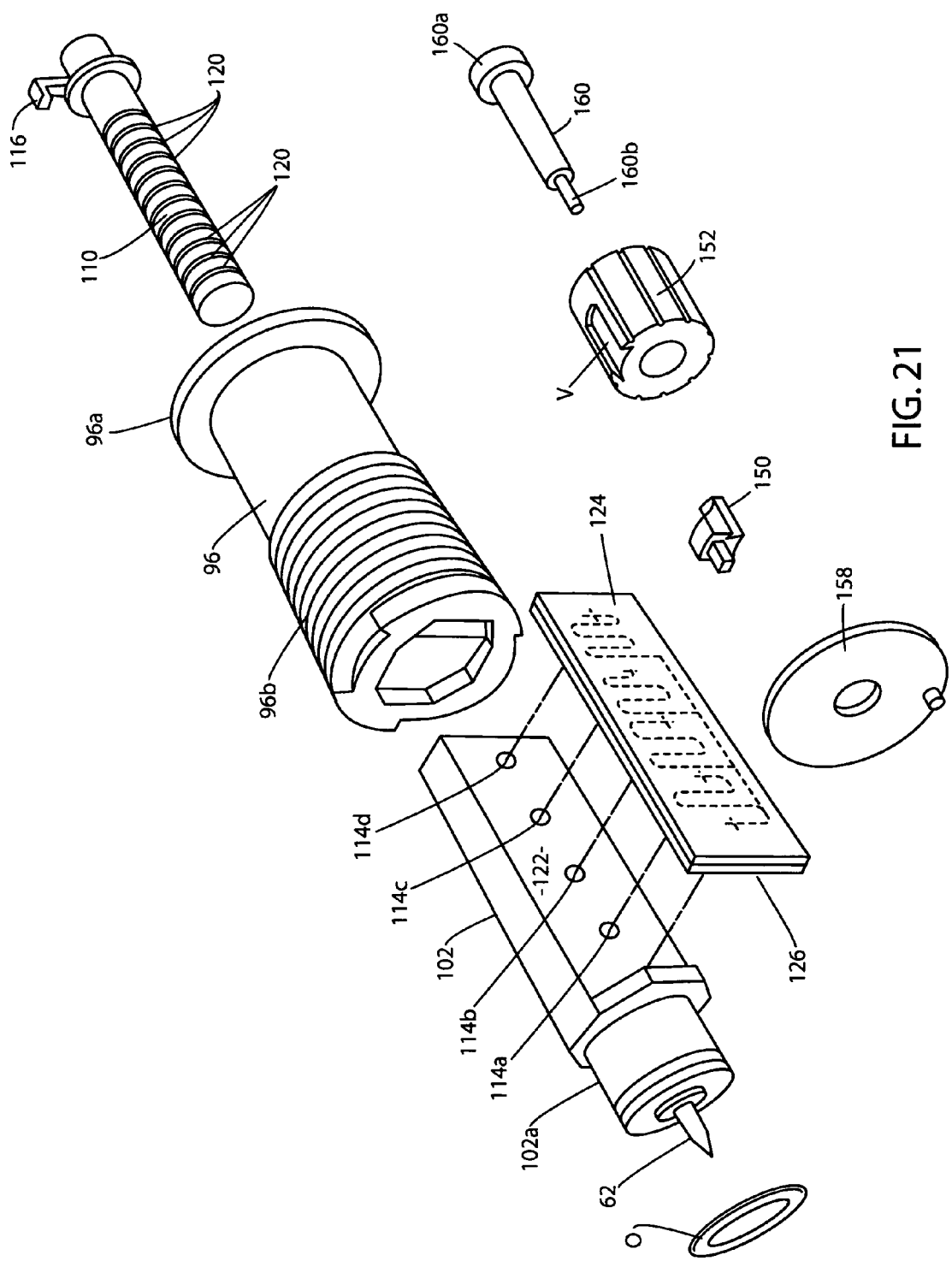
FIG. 21 is an enlarged, generally perspective exploded view of the rate control and advancement housing shown in FIG. 20.
Figure 30:
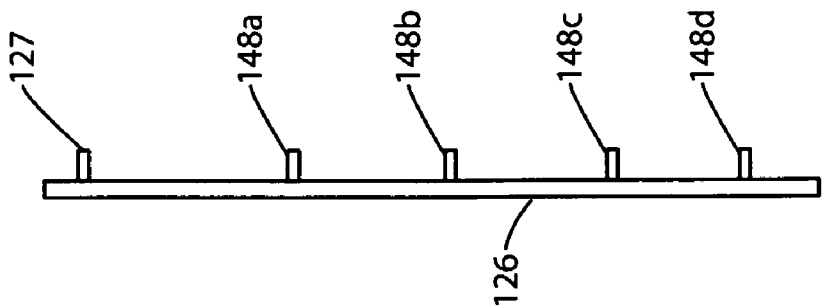
FIG. 30 is a view taken along lines 30-30 of FIG. 29.
Figure 29:
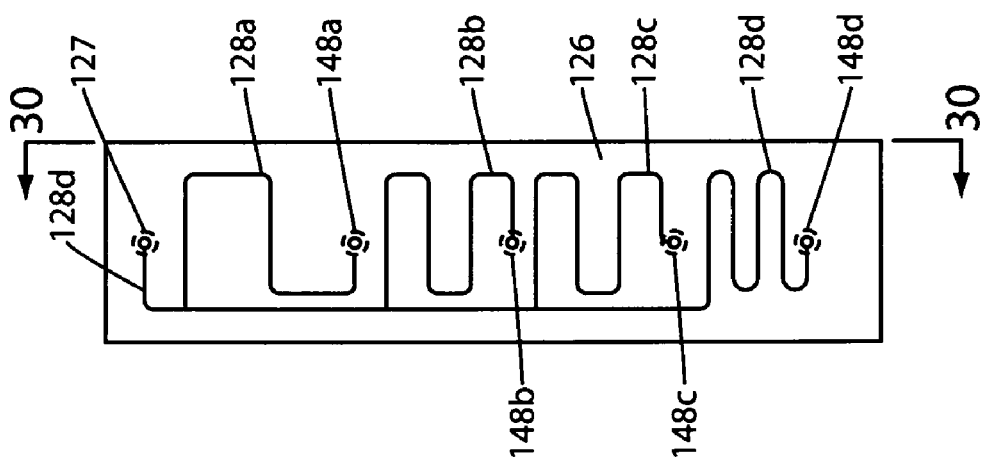
FIG. 29 is a top plan view of the rate control base of the rate control assembly of the apparatus of the invention.
Figure 28:
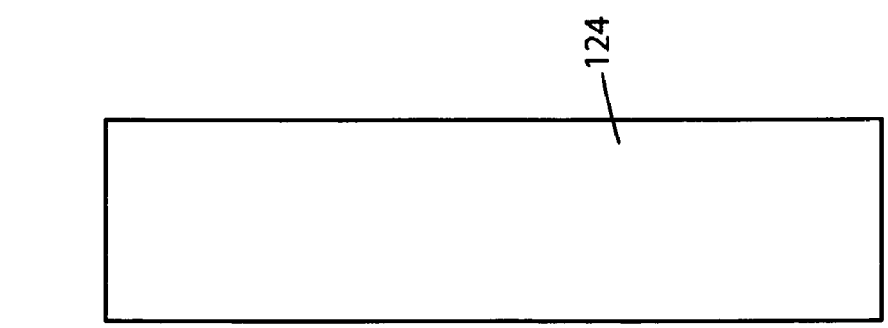
FIG. 28 is a view taken along lines 28-28 of FIG. 27.
Figure 27:
FIG. 27 is a side elevational view of one form of the rate control cover of the rate control assembly of the apparatus of the invention.

As best seen in FIG. 21, body portion 102a of the penetrating assembly 102 is provided with a longitudinally extending, generally planar surface 122 that engages a generally planar shaped rate control plate 126 that forms a part of the important rate control means of the invention for controlling the rate of fluid flow toward the patient. Also forming a part of the rate control means of the invention is a rate control plate 126 that is covered by cover 124 in the manner illustrated in FIGS. 20 and 21. As shown in FIG. 29, rate control plate 126 is provided with an inlet 127 that communicates with a plurality of serpentine micro-channels 128a, 128b, 128c and 128d the purpose of which will presently be described. Micro-channels, which are controllably etched into the rate control plate 126, are in communication with fluid passageway 108. The length, width and depth of the micro-channels determine the rate at which the fluid will flow through the micro-channels toward the patient.

Figure 31:
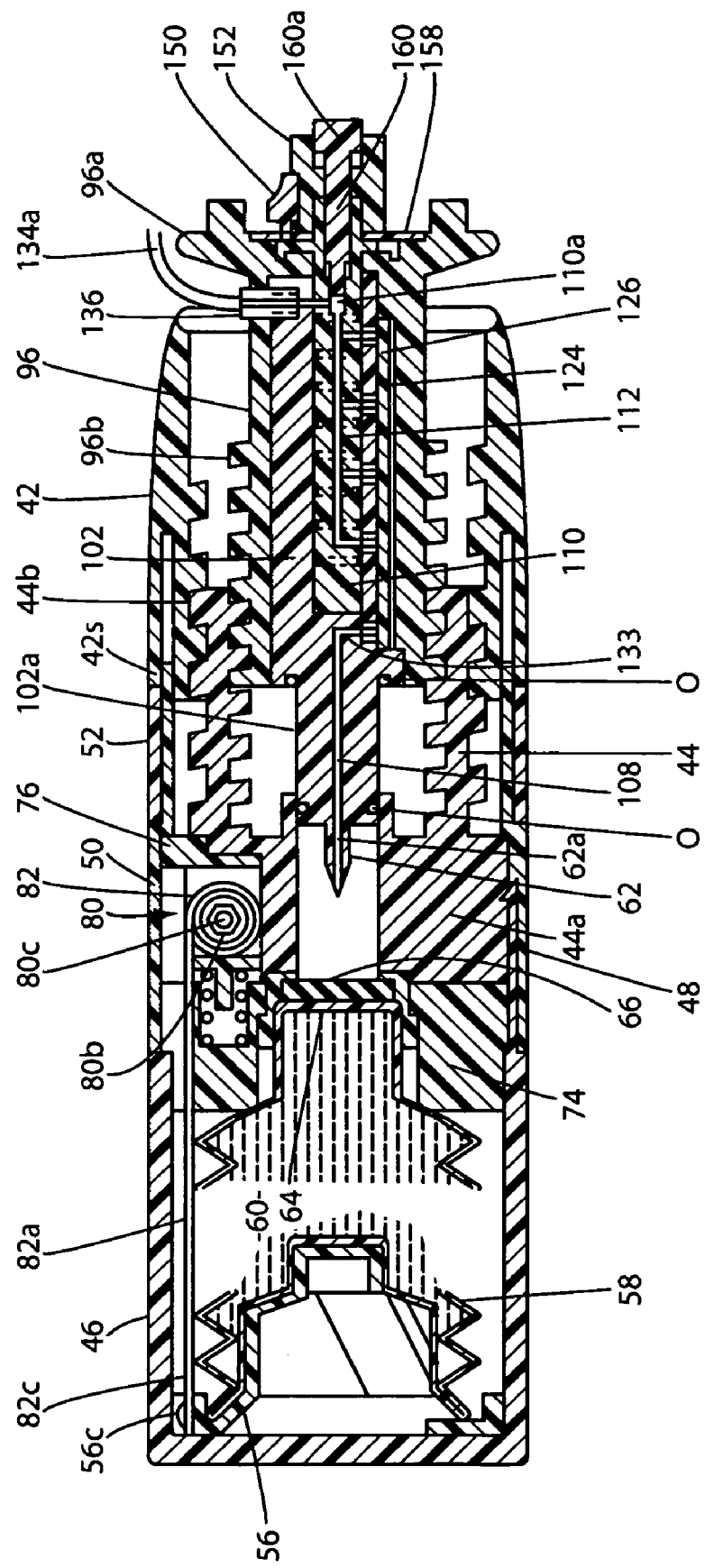
FIG. 31 is a longitudinal cross-sectional view similar to FIG. 2, but showing the multiple rate control assembly of the apparatus rotated into a forward position to expose the administration set.
Figure 36:
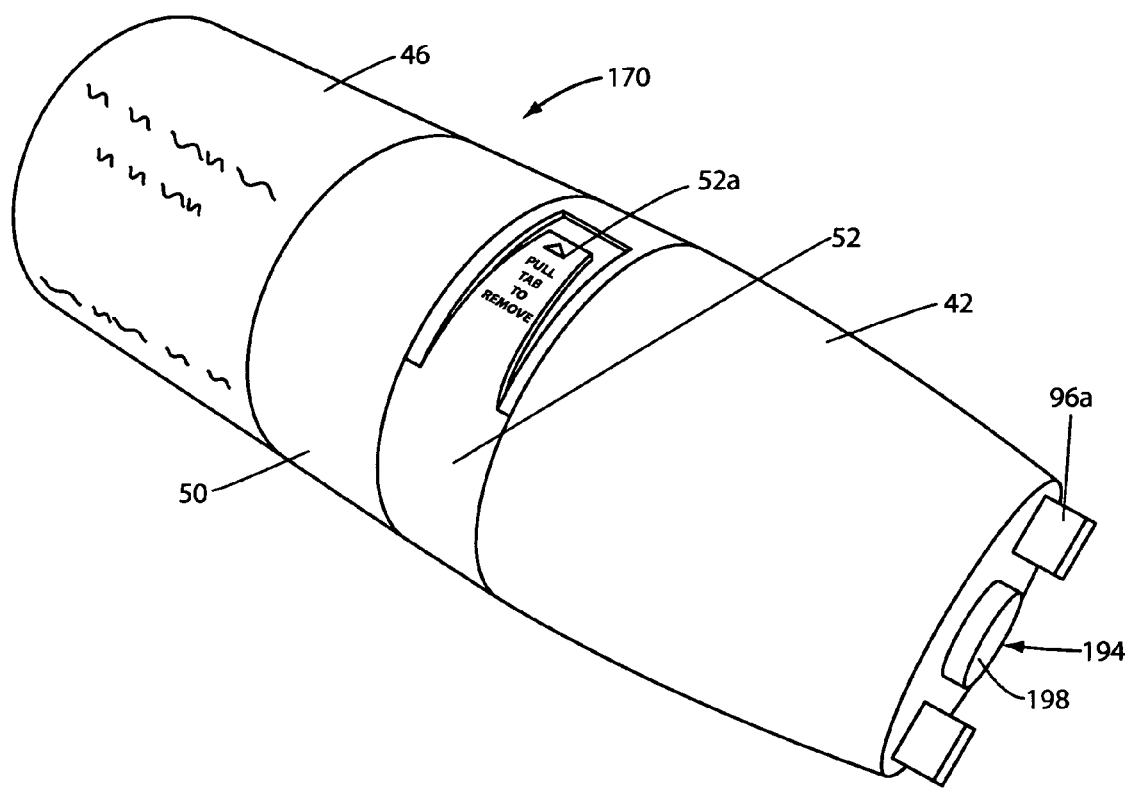
FIG. 36 is a generally perspective view of an alternate form of the fluid dispensing apparatus of the present invention.

In using the apparatus of this latest form of the invention, the first step is to grip the enlarged diameter finger gripping portion 96a of housing 96 and rotate the housing from the position shown in FIG. 2 of the drawings into the extended position shown in FIG. 31 of the drawings. In this position, the administration line 134a of the administration set can be unwrapped from the body of the housing about which it has been coiled into the position shown in FIG. 32 of the drawings. As shown in FIG. 32, the proximal end 133 of administration line 134a is connected to housing 96 by means of a connector 136. Connector 136 is received within an opening 136a provided in housing 96 and within an opening 103 provided in penetrating housing 102. As shown in FIG. 20A, opening 103 communicates with bore 110a of rate control shaft 110. Disposed between the proximal end 133 and the distal end 135 of the administration line is a conventional gas vent and filter 137 and a generally Y-shaped injector site, generally designated by the numeral 138. A luer connector 140 of conventional construction is provided at the distal end 135 of the administration line.

After the administration line has been unfurled into the configuration shown in FIG. 32, the previously mentioned tear strip, or locking band 52, is removed by pulling upwardly and outwardly on the locking band tab 52a (see FIG. 1). Locking band 52 forms a part of the novel locking means of the invention which functions to prevent accidental relative rotation between front housing 42 and internally-externally threaded reservoir spring housing 44. Removal of locking band 52 permits relative rotation between the first, or front, housing 42 and the reservoir spring housing 44 so as to cause the front housing 42 to move rearwardly into the position illustrated in FIG. 32 of the drawings. As the front housing 42 moves rearwardly, the penetrating housing 102 will also move rearwardly causing the penetrating member 62 to penetrate elastomeric member, or pierceable septum 66 and closure wall 64 of the fluid reservoir defining component 60, thereby opening communication between the fluid reservoir 60 and the internal passageway 62a of the penetrating member 62. Penetrating housing 102 is provided with spaced apart O-rings "O" (FIG. 2) to prevent fluid leakage between the moving components.

Rearward movement of the first housing 42 as a result of the relative rotational movement between the first, or front housing 42 and the reservoir spring housing 44 will cause shoulder 42s of first housing 42 to engage the three spring carriage assemblies 76 that house the drum assemblies 80 of the stored energy means and move them rearwardly from the position shown in FIG. 31 and into the position shown in FIG. 32 of the drawings. Movement of the drum assemblies into the position shown in FIG. 32 will cause the release of the variable force springs 82, which will cause the carriage 56 to advance to the position shown in FIG. 32, which, in turn, will cause the collapse of the fluid reservoir 60.

With communication between the fluid reservoir 60 and the internal passageway 62a of the penetrating member 62 having been established, the fluid contained within the fluid reservoir will be expelled from the reservoir and the fluid will flow into the internal passageway 62a of the penetrating member 62. From passageway 62a, fluid will flow into passageway 108, into passageway 133 and into inlet 127 of rate control plate 126 and then into the various circuitous fluid micro-channels 128a, 128b, 128c and 128d formed in the rate control plate (see FIG. 29). As each of the micro-channels fills with the medicinal fluid to be dispensed to the patient, the fluid will flow next into outlet passageways 148a, 148b, 148c and 148d, respectively formed in the rate control plate. Rate control plate 126, which can be constructed from various plastics, is oriented relative to penetrating assembly 102 in the manner depicted in FIG. 21 so that, as will presently be described, longitudinally spaced radial passageways 114e, 114f, 114g and 114h formed in rate control shaft 110 can communicate with outlet passageways 148a, 148b, 148c and 148d respectively.

As illustrated in FIG. 21, a slide lock 150 is carried within a "V" groove formed in a selector knob 152. Upon advancement of the slide lock 150 into a selector knob locking position, the selector knob can be used to controllably rotate rate control shaft 110 so that a selected one of the plurality of longitudinally spaced radial passageways 114e, 114f, 114g and 114h formed in rate control shaft 110 can be brought into communication with a selected one of the outlet passageways 148a, 148b, 148c and 148d formed in the rate control plate. Since the central passageway 112 of the selector member is in fluid communication with the administration set 134 in the manner previously described, the fluid can be delivered to the patient at a selected controlled rate of flow. As best seen in FIGS. 34 and 35, the rate of fluid flow can be selected by rotating the selector knob to the desired flow rate indicated by the indicia 155 imprinted on the rate control indicator plate 158).

Considering now the important disable means of the invention for disabling the apparatus and preventing fluid flow from the reservoir of the device toward the administration set 134 via central passageway 112 of the selector member. In the present form of the invention, rate control shaft 110 of the rate control means is provided with a longitudinally extending bore 110a that slidably receives a disabling shaft 160 having an enlarged diameter head portion 160a. As indicated in the drawings, when the disabling shaft 160 is pushed inwardly from the position shown in FIG. 2 into an inward position, wherein it resides within a cavity 118 provided in the rate control shaft housing 110, the forward portion 160b of the disabling shaft will move into a cavity 110a formed in rate control shaft 110 thereby blocking fluid flow from central passageway 112 toward the administration set and toward the patient. Forward travel of the disabling shaft is stopped when the head portion 160a seats within a cavity 152a formed in selector knobs 152 (see FIG. 20). By stopping fluid flow in this manner, the apparatus is substantially safely disabled until the disabling shaft is once again returned to the starting position shown in FIG. 2 of the drawings.

Turning now to FIGS. 36 through 66, an alternate form of the apparatus of the invention is there shown. This form of the apparatus is similar in many respects to the embodiment illustrated in FIGS. 1 through 36 and like numerals are used in 36 through 66 to identify like components. The primary difference between this alternate embodiment of the invention and the earlier described embodiments resides in the differently configured fluid flow means. In this latest form of the invention, the fluid flow means comprises a fixed rate fluid flow means, rather than a variable rate fluid flow means as described in the embodiment of FIGS. 1 through 36.

Figure 39:
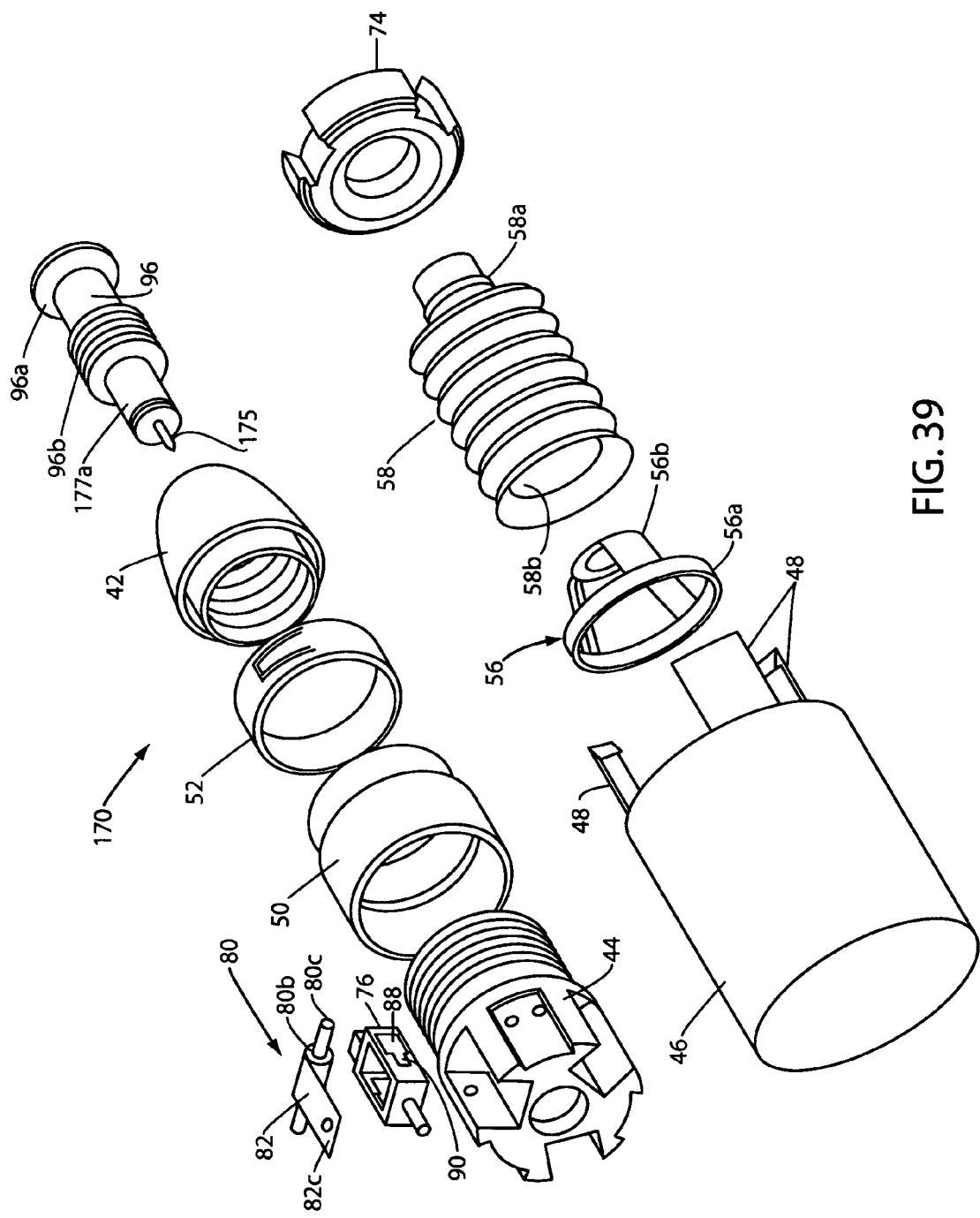
FIG. 39 is a generally perspective, exploded view of the fluid dispensing apparatus shown in FIG. 36.
Figure 40:
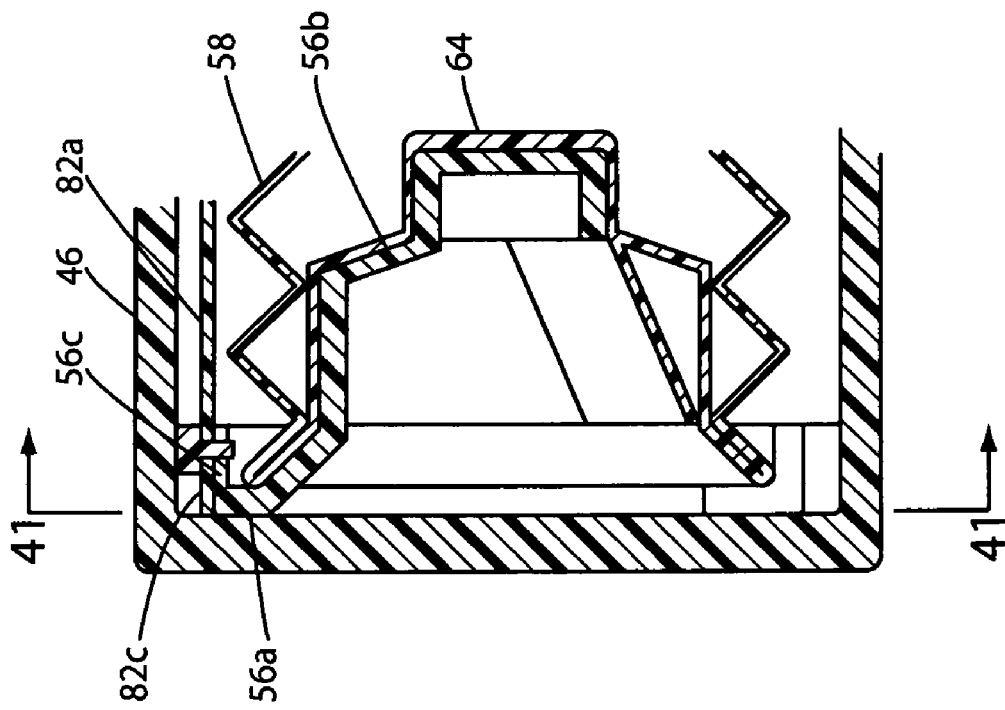
FIG. 40 is a greatly enlarged cross-sectional view of the left-hand portion of the apparatus shown in FIG. 37 of the drawings illustrating the construction of the carriage assembly of the invention.
Figure 41:
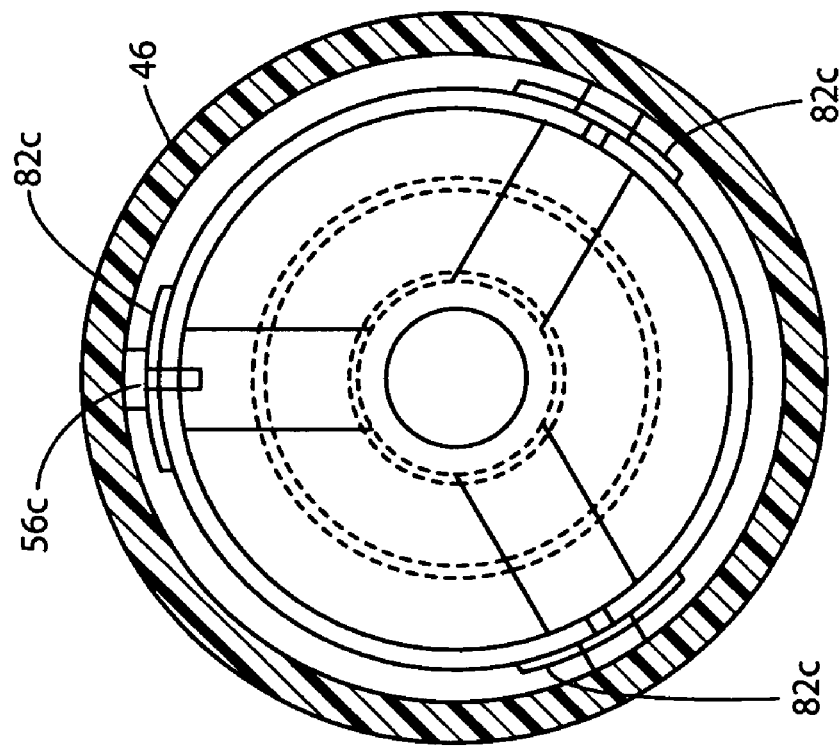
FIG. 41 is a cross-sectional view taken along lines 41-41 of FIG. 40.
Figure 50:
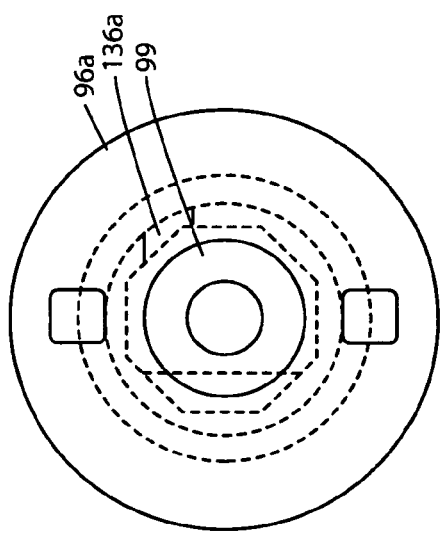
FIG. 50 is a view taken along lines 50-50 of FIG. 48.
Figure 48:
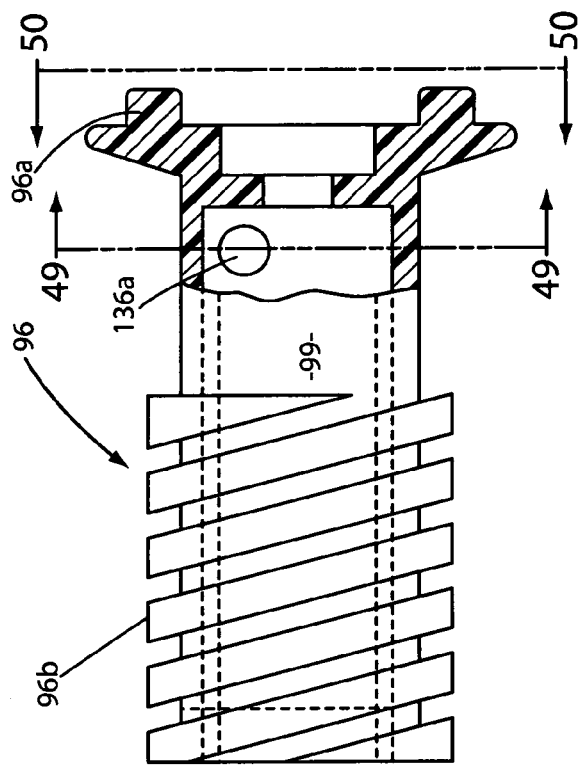
FIG. 48 is a side elevational view partially in cross-section of the rate control advancement housing of this latest form of the invention.
Figure 49:
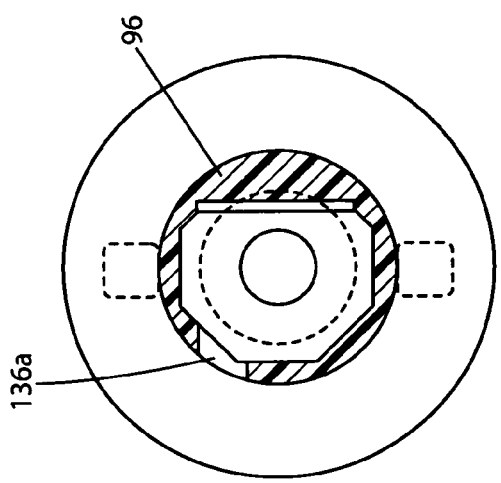
FIG. 49 is a cross-sectional view taken along lines 49-49 of FIG. 48.
Figure 54:
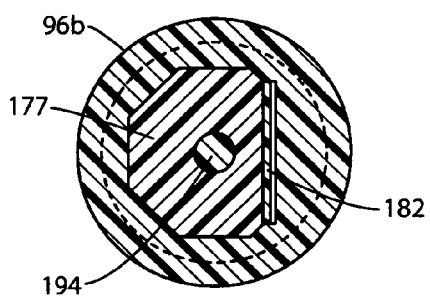
FIG. 54 is a cross-sectional view taken along lines 54-54 of FIG. 51.
Figure 53:
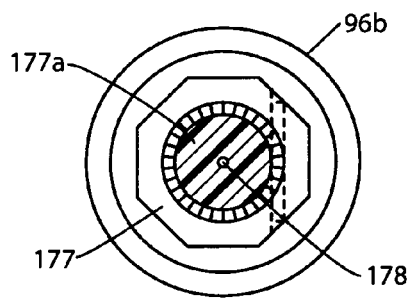
FIG. 53 is a view taken along lines 53-53 of FIG. 51.
Figure 51:
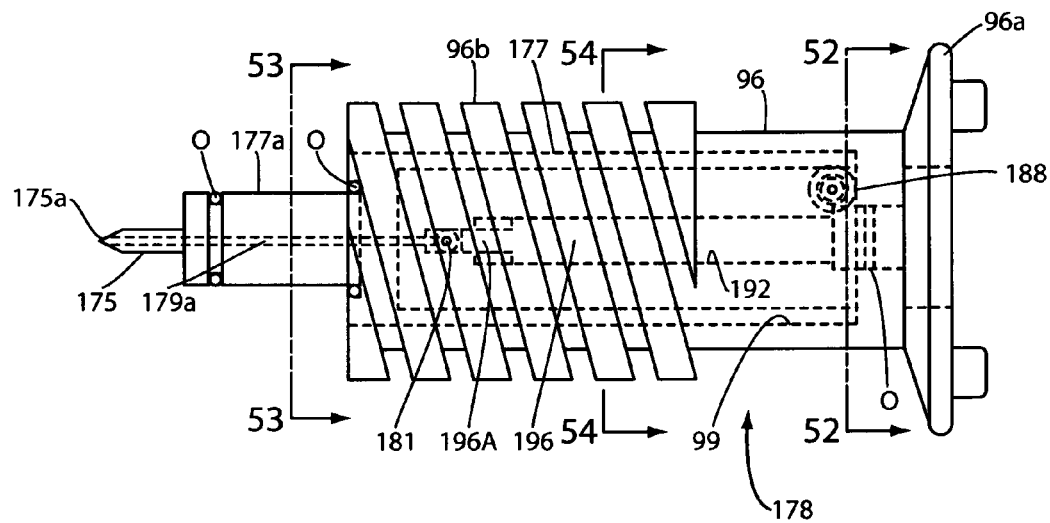
FIG. 51 is a side elevational view of the rate control and advancement housing of this latest form of the invention.

Referring particularly to FIGS. 36 through 40 of the drawings, this alternate form of the fluid dispensing apparatus of the invention for dispensing medicaments to a patient is generally designated by the numeral 170. As best seen in FIGS. 37 and 38, as in the earlier described embodiment, fluid dispensing apparatus 170 here comprises an internally threaded first, or front housing 42, an internally-externally threaded second or reservoir spring housing 44 connected to the internally threaded front housing 42 and a second assembly 46 connected to the internally-externally threaded reservoir spring housing 44 by three circumferentially spaced locking tabs 48 (FIGS. 37 and 39). Disposed between front housing 42 and second assembly 46 is a separator collar 50. Disposed between separator collar 50 and front housing 42 is a tear strip or locking band 52 that functions in the manner previously described.

Housed within second assembly 46 and carried by a carriage 56 is a fluid reservoir defining component, or hermetically sealed collapsible container 58. Carriage 56 as well as collapsible container 58 are substantially identical in construction and operation to those previously described. Operably associated with the carriage 56 for moving it between a first retracted position shown in FIG. 37 and a second advanced, fluid delivery position shown in FIG. 68 is a novel stored energy means, which, as before, comprises three drum assemblies 80 about which a portion of three elongated springs 82 are wound. Elongated springs 82, which are substantially identical in construction and operation to those previously described, comprise tightly coiled wound bands of pre-hardened spring steel or stainless steel strip with built-in curvature so that each turn of the strip wraps tightly on its inner neighbor (see FIGS. 37 and 38).

As in the earlier described embodiment of the invention, the fluid medicament reservoir 60 of collapsible container 58 is accessible via a penetrating member 175 which forms the inlet to the fluid delivery and control assembly of the invention, the character of which will presently be described. More particularly, penetrating member 175, which forms a part of the penetrating assembly 177 of the invention, is adapted to pierce a top, or closure wall 64 of the reservoir defining component 58 as well as a pierceable septum 66 (FIGS. 43 and 44) which is secured in position over closure wall 64 by means of a closure cap 70 that is affixed to the neck portion 58a of the reservoir defining component.

As before, the reservoir defining component 58 is held in position within housing 46 by means of a ring like member 74 that is disposed in engagement with internally-externally threaded reservoir spring housing 44 in the manner shown in FIG. 38. Ring like member 74 functions to partially support three circumferentially spaced spring carriage assemblies 76, each of which houses a portion of the previously mentioned stored energy means of the invention. More particularly, the spring carriage assemblies 76 house the drum assemblies 80 of the stored energy means about which a portion of the elongated springs 82 of the stored energy means are wound. The spring carriage assemblies 76 are also substantially identical in construction and operation to those previously described and, as previously discussed, when the spring housings are urged into a second, rearward position as a result of relative rotation of housings 42 and 44, drum 82 is free to rotate so that the spring can be wound about the drum thereby urging the carriage 56 forwardly of the apparatus.

Considering next the fluid delivery and control means of this latest form of the invention, this important means, which functions to control the flow of fluid from the fluid reservoir of the collapsible container toward the patient, comprises a flow control assembly generally designated in the drawings by the numeral 177. Assembly 177 includes a rate control advancement housing 96 that is substantially identical in construction and operation to that previously described. As before, rate control advancement housing 96 includes an enlarged diameter finger-gripping portion 96a and a reduced diameter externally threaded portion 96b. Externally threaded portion 96b is provided with central bore 99 that receives a penetrating-rate control assembly 177 which includes penetrating component 177a having a fluid passageway 175a and a penetrating member 175 that has a fluid passageway 175a that is in communication with fluid passageway 178. Penetrating-rate control assembly 177 also includes a rate control component 177b having a longitudinally extending, generally planar rate control plate receiving surface 180, having a fluid outlet 181 that is in communication with fluid passageway 178 (FIG. 56).

Figure 52:
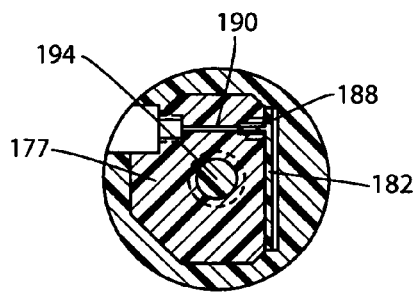
FIG. 52 is a cross-sectional view taken along lines 52-52 of FIG. 51.
Figure 55:
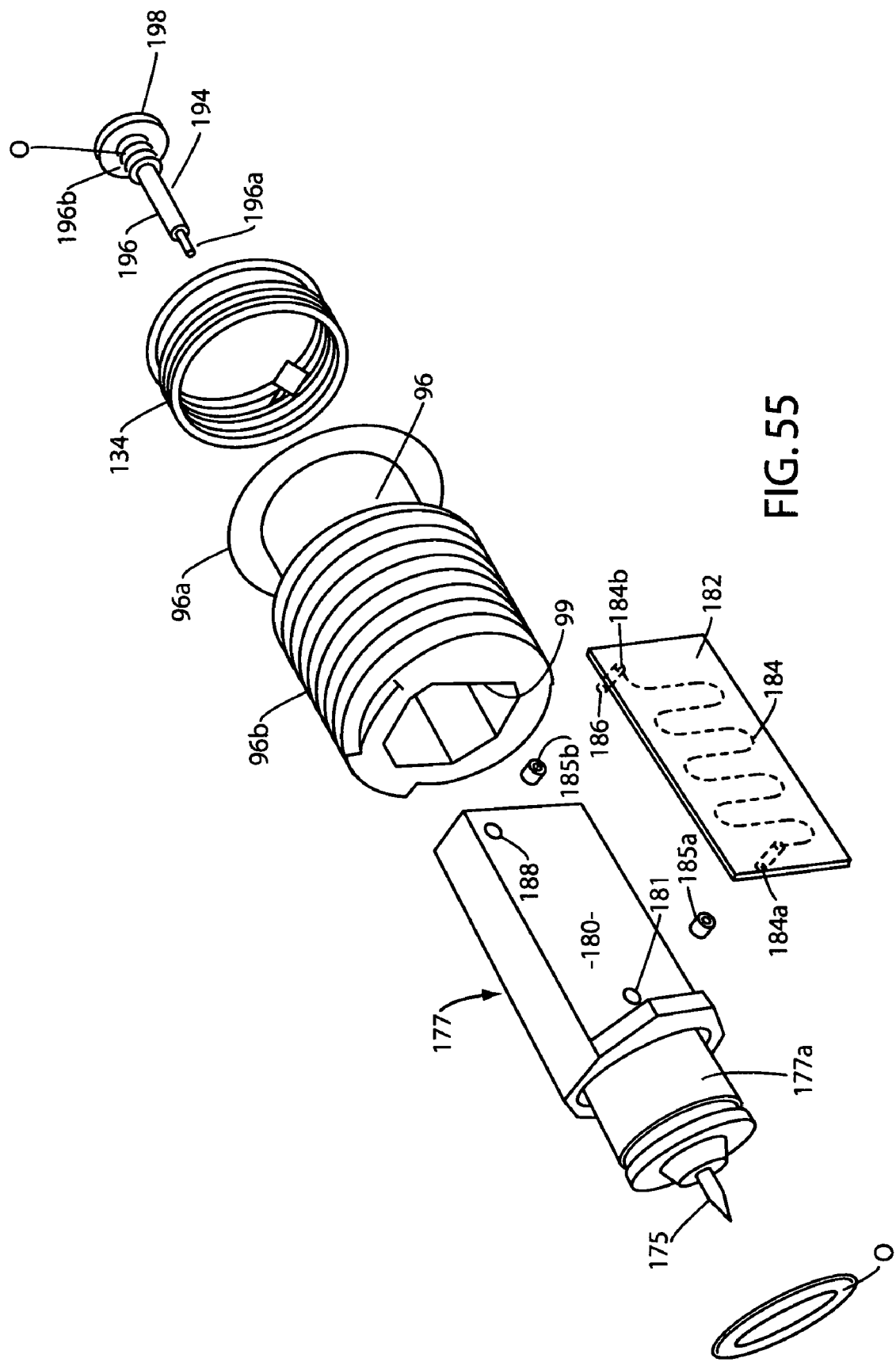
FIG. 55 is an enlarged, generally perspective exploded view of the rate control and advancement housing of this latest form of the invention.
Figure 61:
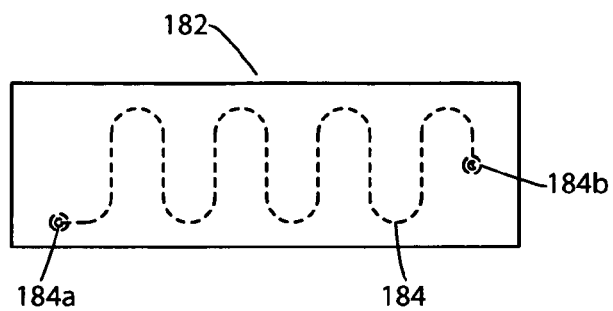
FIG. 61 is a view taken along lines 61-61 of FIG. 60.
Figure 60:
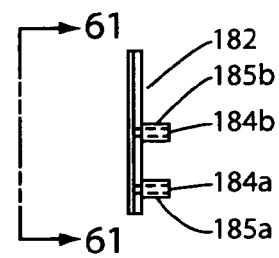
FIG. 60 is a side elevational view of the rate control assembly of this latest form of the invention.
Figure 62:
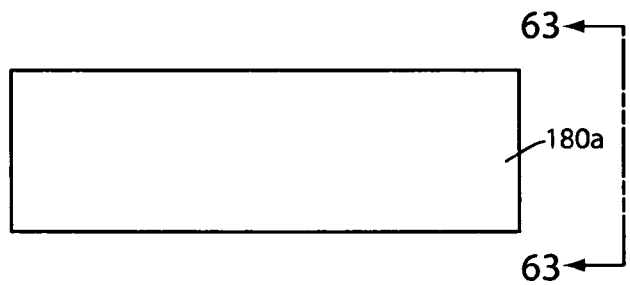
FIG. 62 is a side elevational view of the rate control cover of the rate control assembly shown in FIG. 60.
Figure 63:
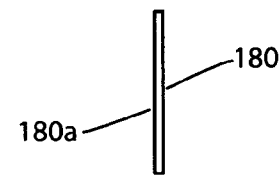
FIG. 63 is a view taken along lines 63-63 of FIG. 62.
Figure 64:
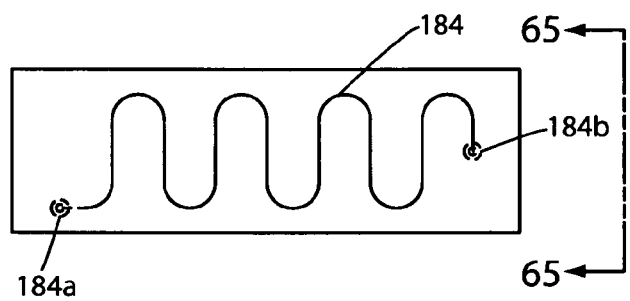
FIG. 64 is a side elevational view of the rate control base of the rate control assembly.
Figure 65:
FIG. 65 is a view taken along lines 65-65 of FIG. 64.

Penetrating rate control assembly 177 further includes the important rate control means of the invention for controlling the rate of fluid flow toward the patient. The rate control means of the invention here comprises a rate control plate 182 that is disposed in engagement with rate control plate receiving surface 180 of rate control cover 180a. Rate control plate 182 is provided with a serpentine micro-channel 184 which is controllably etched into the rate control plate 182. The length, width and depth of micro-channel 184 determine the rate at which the fluid will flow through the micro-channel toward the patient. Micro-channel 184 has an inlet 184a that is in communication with outlet 181 of rate control plate receiving surface 180 via a connector port 185a and an outlet 184b that is in communication with an inlet 188 formed in rate control plate receiving surface 180 via a connector port 185b. Inlet 188 is, in turn, in communication the administration set 134 via an outlet passageway 190 formed in penetrating rate control assembly 177 (FIG. 52).

The rate control component 177b of penetrating rate control assembly 177 is also provided with a central bore 192 that receives the disabling assembly 194 of this latest form of the invention. Disabling assembly 194 here comprises an elongated shaft 196 having a reduced diameter portion 196a and an enlarged diameter portion 196b. Connected to enlarged diameter portion 196b is a pusher head 198 that enables the user of the device to push the disabling assembly inwardly from the position shown in FIG. 68 of the drawings to an inward position wherein reduced diameter portion 196*a* enters a small bore 200 formed in rate control component 177 thereby blocking fluid flow through passageway 178 and in so doing disabling the apparatus.

In using the apparatus of this latest embodiment, after communication between the fluid reservoir 60 and the internal passageway 175*a* of penetrating member 175 has been established in the manner previously described by removing the tear strip and causing relative rotation between the front housing 42 and the reservoir spring housing 44, the fluid contained within the fluid reservoir will be expelled from the reservoir and the fluid will flow into the internal passageway 175*a* of the penetrating member 175. From passageway 175*a*, fluid will flow into passageway 178 of penetrating assembly 177, into inlet 184*a* of rate control fluid micro-channel 184. The fluid will then flow at a controlled rate through microchannel 184, outwardly of outlet 184*b*, into flow channel 190 and then onward to the patient via the administration set 134. Once again, O-rings "O" are provided on the penetrating member as indicated in FIG. 37.

Having now described the invention in detail in accordance with the requirements of the patent statues, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for dispensing medicaments to a patient comprising:
   (a) a first assembly including first and second threadably interconnected housings and a rate control assembly carried by said second housing for controlling the rate of flow of medicaments to the patient; and
   (b) a second assembly connected to said first assembly, said second assembly comprising:
      (i) a carriage movable between a first retracted position and a second advanced, fluid delivery position;
      (ii) a fluid reservoir defining component carried by said carriage, said fluid reservoir defining component comprising collapsible container having a pierceable top wall and a reservoir for containing a medicinal fluid to be delivered to the patient;
      (iii) stored energy means operably associated with said carriage for moving said carriage between said first retracted position and said second advanced position to controllably collapse said collapsible container, said stored energy means comprising a plurality of springs, each of said plurality of variable force springs comprising a drum assembly and a band of material wound about said drum assembly; and
      (iv) spring retaining means operably associated with said plurality of variable force springs for initially retaining said plurality of variable force springs in an extended position and then, upon rotation of said first assembly relative to said second assembly to permit said variable force springs to retract.

2. The apparatus as defined in claim 1 in which said reservoir defining component comprises an integrally formed, hermetically sealed container that includes a front portion, a rear, inwardly extending, ullage defining wall portion and a collapsible accordion-like, continuous, uninterrupted side wall that interconnects said front and rear portions of said sealed container.

3. The apparatus as defined in claim 1 in which said first assembly further includes a penetrating member carried by said second housing of said first assembly for piercing said pierceable top wall of said collapsible container.

4. The apparatus as defined in claim 1 in which said rate control assembly controls the rate of flow of medicaments to the patient at a variable rate.

5. The apparatus as defined in claim 1 in which said rate control assembly controls the rate of flow of medicaments to the patient at a fixed rate.

6. The apparatus as defined in claim 1 in which said rate control assembly comprises a generally planar rate control plate including a generally planar surface having at least one micro-channel formed therein.

7. The apparatus as defined in claim 1 in which said apparatus further includes a locking band disposed between said first and second assemblies for preventing rotation of said first assembly relative to said second assembly.

8. The apparatus as defined in claim 1 in which each of said plurality of variable force springs comprises a drum assembly and a band of material wound about said drum assembly in predetermined varying degrees of tightness.

9. An apparatus for dispensing medicaments to a patient comprising:
   (a) a first assembly including first and second threadably interconnected housings and a rate control assembly carried within said second housing for controlling the rate of flow of medicaments to the patient, said rate control assembly comprising a generally planar rate control plate including a generally planar surface having at least one micro-channel etched therein; and
   (b) a second assembly connected to said first assembly, said second assembly comprising:
      (i) a carriage movable between a first retracted position and a second advanced, fluid delivery position;
      (ii) a fluid reservoir defining component carried by said carriage, said fluid reservoir defining component comprising an integrally formed, hermetically sealed container having a pierceable top wall and including a front portion, a rear, inwardly extending, ullage defining wall portion and a collapsible accordion-like, continuous, uninterrupted side wall that interconnects said front and rear portions of said sealed container collapsible container;
      (iii) stored energy means operably associated with said carriage for moving said carriage between said first retracted position and said second advanced position to controllably collapse said collapsible container, said stored energy means comprising a plurality of variable force springs, each of said plurality of variable force springs comprising a shaft and a band of material wound about said shaft; and
      (iv) spring retaining means operably associated with said plurality of variable force springs for initially retaining said plurality of variable force springs in an extended position and then, upon rotation of said first assembly relative to said second assembly to permit said variable force springs to retract.

* * * * *